United States Patent [19]
Carrino et al.

[11] Patent Number: 5,573,907
[45] Date of Patent: Nov. 12, 1996

[54] DETECTING AND AMPLIFYING TARGET NUCLEIC ACIDS USING EXONUCLEOLYTIC ACTIVITY

[75] Inventors: John J. Carrino, Gurnee, Ill.; Uwe Spies, Limburg, Germany; Laurie A. Rinehardt, Kenosha, Wis.; Edward K. Pabich, Chicago, Ill.

[73] Assignee: Abbott Laboratories, Abbott Park, Ill.

[21] Appl. No.: 101,877

[22] Filed: Aug. 4, 1993

Related U.S. Application Data

[63] Continuation-in-part of Ser. No. 925,402, Aug. 3, 1992, abandoned, which is a continuation-in-part of Ser. No. 634,771, Jan. 9, 1991, abandoned, which is a continuation-in-part of Ser. No. 470,674, Jan. 26, 1990, abandoned.

[51] Int. Cl.$^6$ .............. C12Q 1/68; C12P 19/34; C07H 21/04
[52] U.S. Cl. .......... 435/6; 435/91.51; 435/91.52; 435/91.31; 536/24.3
[58] Field of Search ............ 435/6, 91.2, 91.31, 435/91.52, 6, 91.1; 935/77, 78; 536/22.1, 24.3, 24.33, 25.3, 25.32

[56] References Cited

U.S. PATENT DOCUMENTS 4,851,331  7/1989  Vary et al. .................. 435/6

FOREIGN PATENT DOCUMENTS 0246864  5/1987  European Pat. Off. .
0439182  7/1991  European Pat. Off. .

OTHER PUBLICATIONS

Murakami et al Nucleic Acid Research 1991 19: 4097–4102.
Howard et al Proc Natl Acad Sci, USA Biochemistry (1991) 88: 7276–7280.
Habraken et al., "Chromatin 3'-phosphatase/5'-OH kinase cannot transfer phosphate from 3' to 5' across a strand nick in DNA", Nucleic Acids Research, vol. 14, No. 20, issued 1986.
Brutlag et al., "Enzymatic Synthesis of Deoxyribonucleic Acid", J. Biol. Chem., vol. 247, No. 1, pp. 241–248, issued 10 Jan. 1972.
Wu et al., "The ligation amplification reaction (LAR)–amplification of specific DNA sequences using sequential rounds of template–dependent ligation", Genomics 4. pp. 560–569 (1989).
Bailey et al., Biochem. J., 259 (1989) pp. 761–768.

Primary Examiner—W. Gary Jones
Assistant Examiner—Carla Myers
Attorney, Agent, or Firm—Thomas D. Brainard; Paul D. Yasger

[57] ABSTRACT

The present invention relates to improved LCR amplification schemes using at least one downstream probe modified at its 5' end to reduce or eliminate target independent amplification. The different modified probes, and kits containing them are also presented. Also presented is a method for detecting differences in nucleic acid sequences, with reduced target independent amplification, using the modified probes.

59 Claims, 7 Drawing Sheets

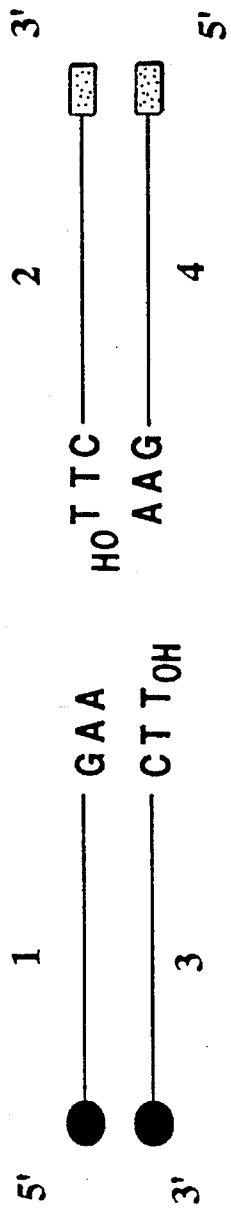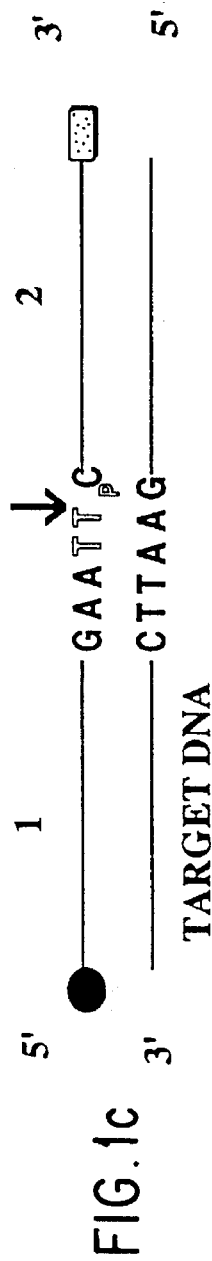

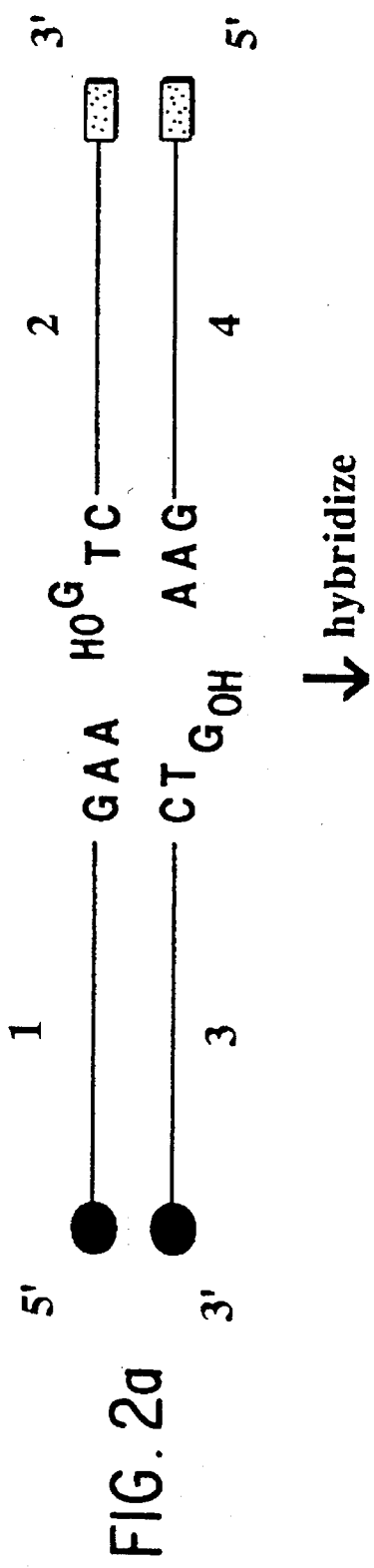
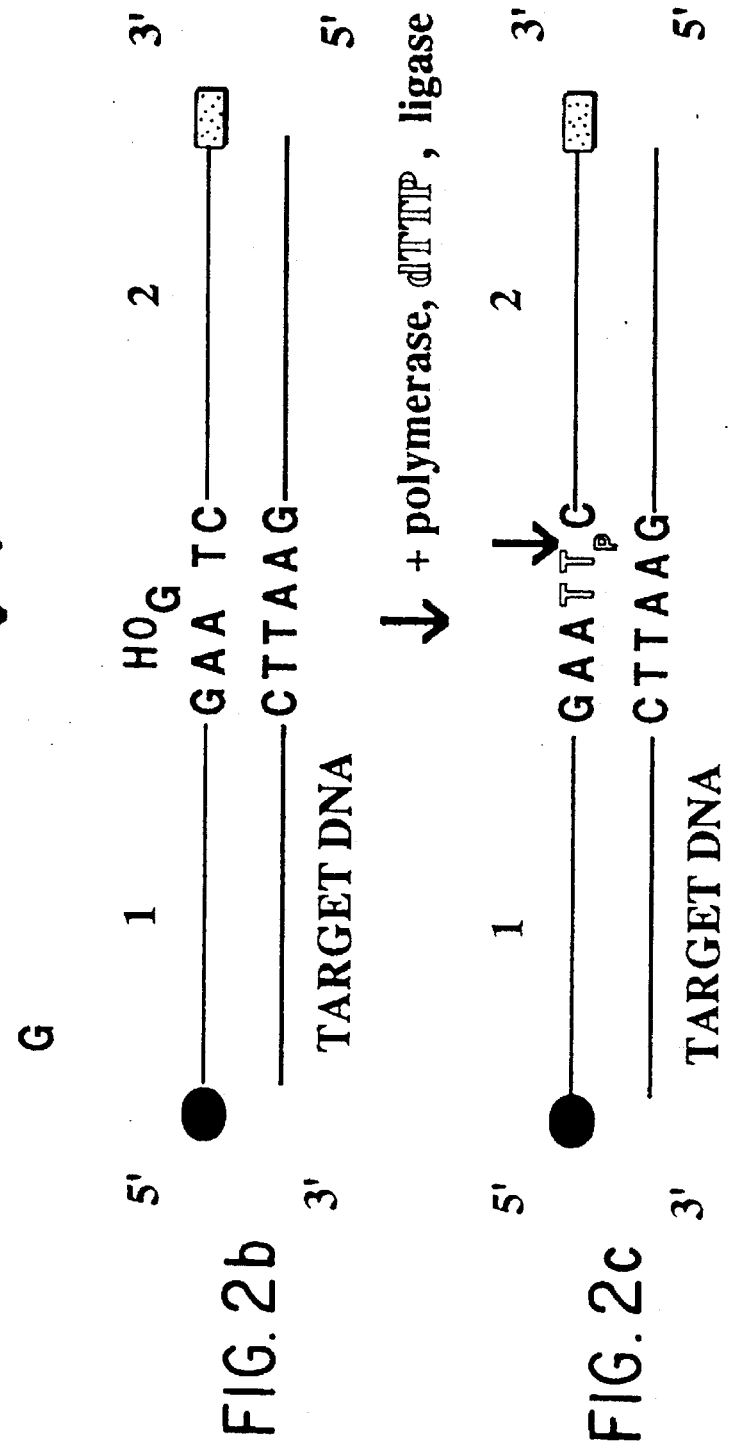
FIG. 2a
FIG. 2b
FIG. 2c

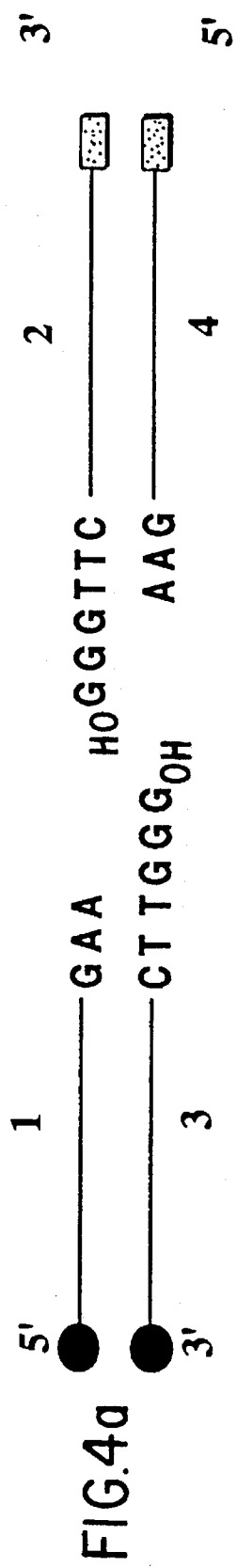
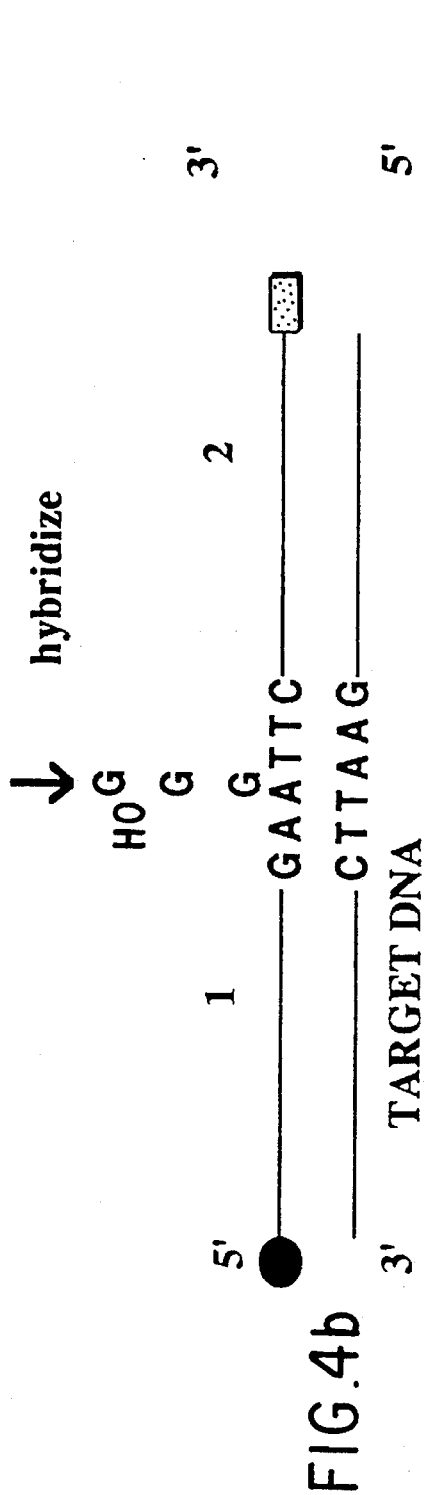
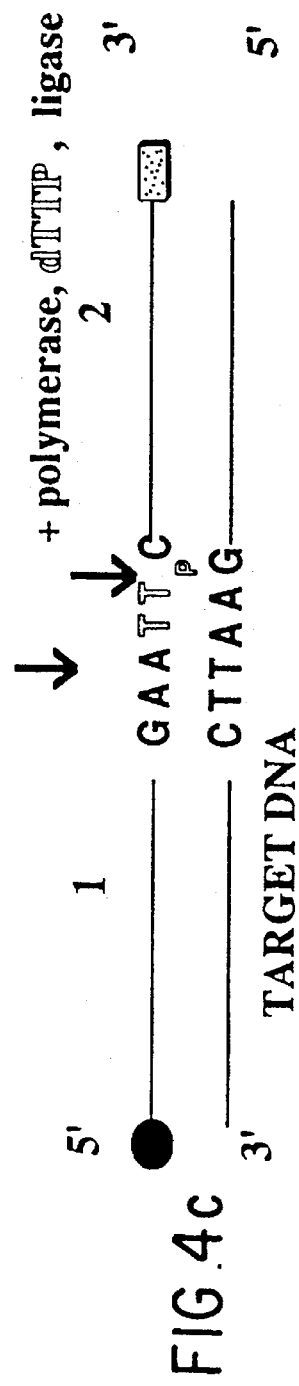
FIG.4a
FIG.4b
FIG.4c

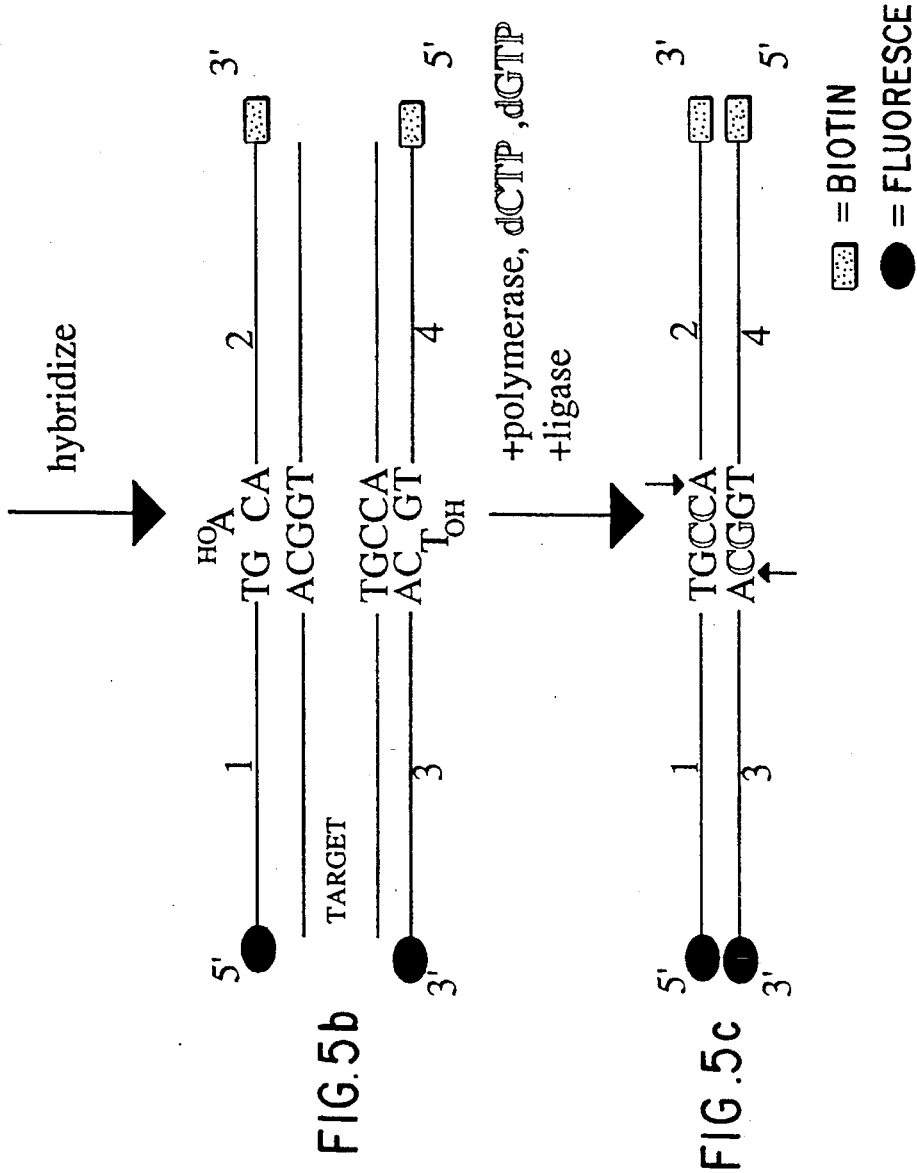

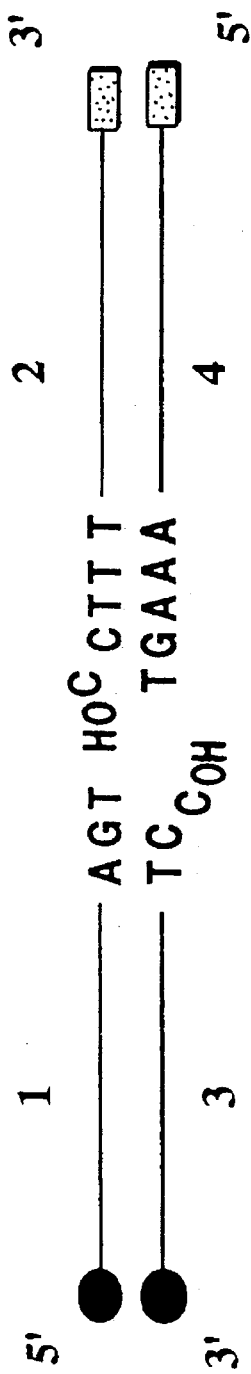
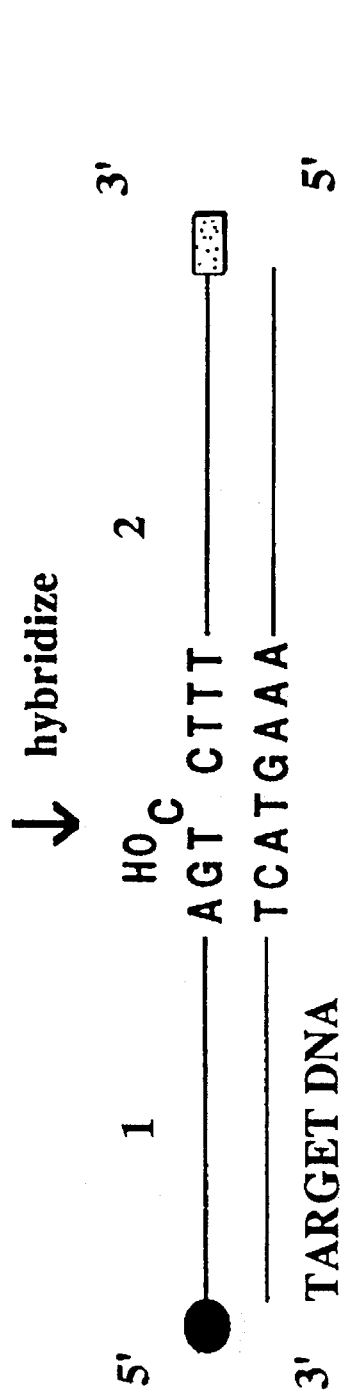
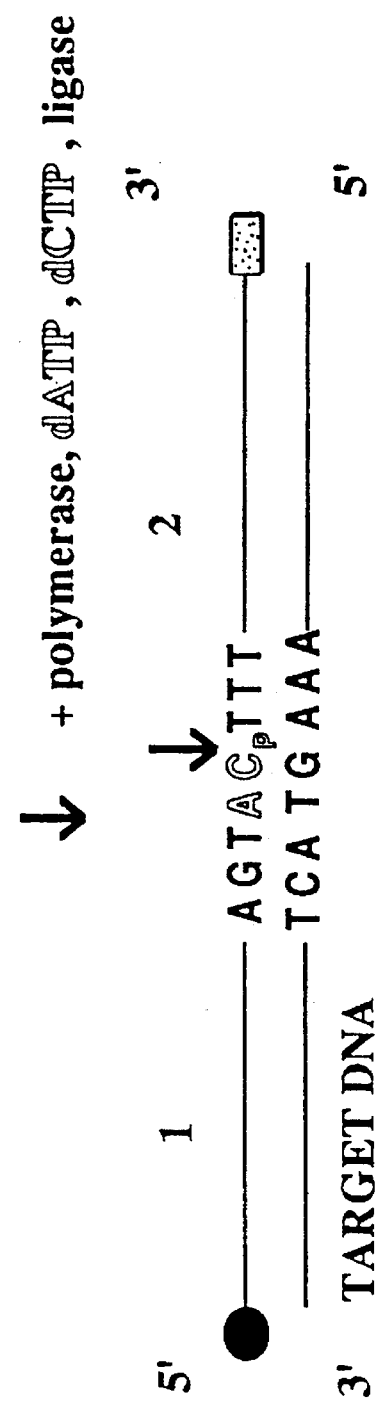

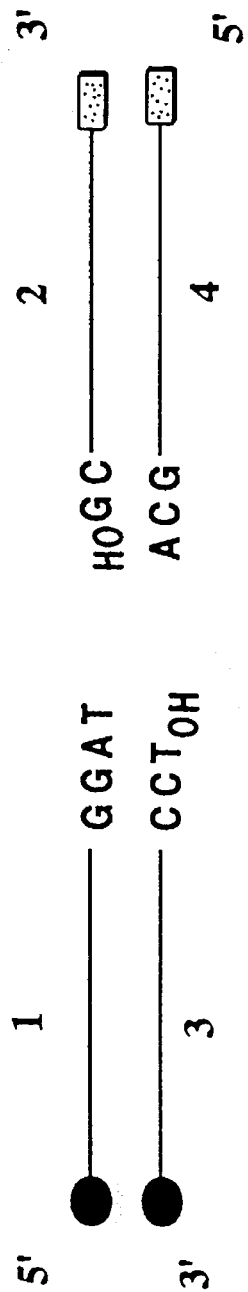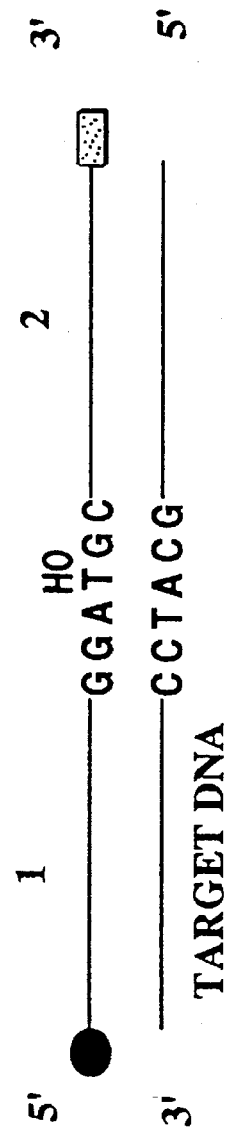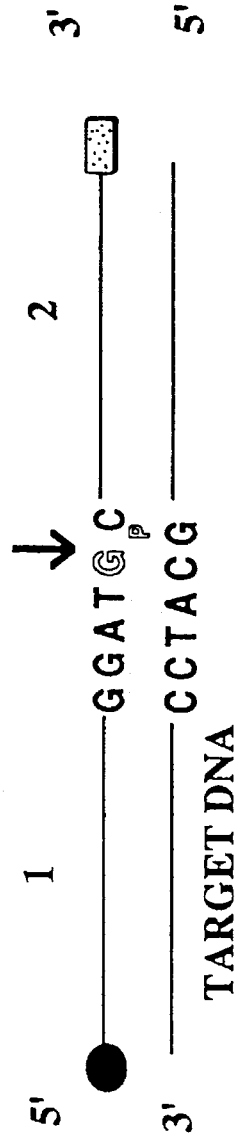

DETECTING AND AMPLIFYING TARGET NUCLEIC ACIDS USING EXONUCLEOLYTIC ACTIVITY

This patent application is a continuation-in-part of U.S. Ser. No. 07/925,402, filed Aug. 3, 1992 now abandoned; which is a continuation-in-part of U.S. Ser. No. 07/634,771, filed Jan. 9, 1991 now abandoned; which is a continuation-in-part of U.S. Ser. No. 07/470,674, filed Jan. 26, 1990 now abandoned. All patent application mentioned above enjoy common ownership with this application and are incorporated herein in their entirety. Ser. No. 07/470,674 is now abandoned.

FIELD OF THE INVENTION

This invention relates generally to nucleic acid amplification techniques and, more specifically, to the reduction and preferably elimination of target independent background amplification in assays utilizing the ligase chain reaction (LCR). The invention also relates to the identification of differences in target nucleic acid sequences.

BACKGROUND

The ligase chain reaction (LCR) is a method for amplifying a specific nucleic acid sequence (target) in a sample. LCR can be used to detect single or double stranded DNA targets. Typically, two ligatable pairs of probes are employed in excess over the target, one pair of the probes are hybridizable to the other. The target DNA is first denatured (if double stranded) to allow for the hybridization of the ligatable probe pairs to their respective complementary strands. The hybridized probes are then ligated by DNA ligase. Next, the ligated probes are dissociated from the target and function as target sequences themselves. By repeated cycles of hybridization and ligation, amplification of the target sequence is achieved. The process of LCR is described in the literature, including EP-A-320,308, EP-A-439,182, EP-A-336,731, WO 89/09835, WO 89/12696, and WO 90/01069 among others.

A common problem for LCR is non-specific (i.e. target independent) amplification which can lead to false positive results. This can occur, for example, when a pair of adjacent LCR probes are ligated to each other in the absence of the target. Since LCR probes are typically used in high concentration relative to the target the possibility of target independent ligation is great, and there is a comensurate need to overcome this concern.

Methods for reducing target independent ligation events have been described. For example, EP-A-439,182 describes a variation of LCR wherein one of the probes of the ligatable pair is modified so that it cannot be ligated until a correction event takes place. Correction events take place only when the probe is hybridized to target. Specifically, this application describes modifications to the 3' ends of the upstream probe, where upstream refers to the probes whose 3' ends participate in the ligation reaction. Disclosed modifications are a 3' blocking group, such as phosphate; a 3' overhang of ribonucleotides (on a deoxyribonucleotide probe); 3' overhangs including an abasic site; and 3' gaps which must be filled in to render the probes adjacent and ligatable. None of the disclosed embodiments involve modifications of the 5' end of the downstream probe.

SUMMARY OF THE INVENTION

The invention provides methods for reducing, and preferably eliminating, target independent amplification by employing modified downstream probes with 5' ends that are incapable of being ligated absent a target-dependent correction step; i.e. these ends can be ligated only after they have been enzymatically degraded following the hybridization of the probe to a target nucleic acid sequence.

Thus, the method of the invention comprises the steps of:

(a) under hybridizing conditions exposing a sample suspected of containing the target nucleic acid sequence in single stranded form to an excess of a first set of oligonucleotides comprising a first upstream probe and a first downstream probe, both probes having sequences substantially complementary to portions of a target nucleic acid sequence, the 3' terminus of the first upstream probe hybridizing proximate to the 5' terminus of the first downstream probe, wherein the 5' end of the first downstream probe is modified to be ligation incompetent absent correction, thereby hybridizing the first set of oligonucleotides to the target nucleic acid sequence, if present;

(b) correcting the 5' end of the downstream probe substantially only when the downstream probe is hybridized to target, said correction including exonucleolytic degradation of said 5' end, whereby the correction renders this 5' end ligation competent;

(c) ligating the corrected downstream probe to the upstream probe to form a ligated product; and (d) determining to what extent the correction and ligation steps occur as a measure of the target nucleic acid in the sample.

The means for rendering the 5' end of the downstream probe ligation incompetent fall into two general groups. First, a ligation incompetent end is obtained by a non-phosphorylated 5' terminus, which is corrected by cleaving the terminal nucleosides to create a new 5' phosphorylated terminus on said downsteam probe. Second, a ligation incompetent end is obtained selecting a probe sequence which includes at least one nucleotide base in said 5' end which is mismatched with respect to the target sequence to which it hybridizes. This modification is corrected by cleaving the mismatched nucleotide to create a new 5' phosphorylated terminus on said downsteam probe. Such a mismatched nucleotide base may be directly at the 5' terminus or it may be internal, i.e. from 1 to about 5 residues from the 5' terminus. In correcting mismatched bases, it has been found that the matched base adjacent the mismatch on its 3' side is also cleaved.

In some embodiments, degradation of the 5' end is stopped at the point where the 3' end of the upstream probe is abutting, i.e. adjacent. In other embodiments degradation continues beyond this point and the upstream probe is also extended to abut the newly created 5' phosphorylated terminus of the corrected downstream probe. This cleaving and extending activity is nicely performed by certain polymerases having 5' to 3' exonuclease activity, but the two processes may be performed by distinct reagents as well.

The ligation events, which are dependent on the presence and/or amount of target in the sample, may be determined by assaying for the ligation product, e.g. by its larger molecular weight or by combination of distinctly labeled probes into a bi-labeled molecule; or by monitoring the release of cleaved fragments from the corrected 5' ends, e.g. by fluorescence polarization or fluorescence quenching.

Preferably, the amount of target sequence in the sample is increased prior to detection, by including an excess of a second set of oligonucleotides comprising a second upstream probe and a second downstream probe, both probes having sequences substantially complementary to the first downstream probe and first upstream probes, respectively (and therefore also complementary to the complement of the target sequence), the 3' terminus of the second upstream probe being hybridized proximate to the 5' terminus of the second downstream probe. In such a case, amplification is effected by repeating the hybridization, correction and ligation steps (a–c) several times. Repetition is generally from 10 to about 50 cycles. In the amplification variation the second downstream probe may but need not also carry a 5' modification making it ligation incompetent. If it does, the modification may be the same or different than that of the first downstream probe. Correction, ligation and detection are the same as before.

Another aspect of the invention provides compositions comprising modified probes as above. Such compositions comprise:

(a) a first set of oligonucleotides comprising a first upstream probe and a first downstream probe, both probes having sequences substantially complementary to portions of a target nucleic acid sequence, the 3' terminus of the first upstream probe hybridizing proximate to the 5' terminus of the first downstream probe; and (b) a second set of oligonucleotides comprising a second upstream probe and a second downstream probe, both probes having sequences substantially complementary to the first downstream probe and first upstream probes, respectively, the 3' terminus of the second upstream probe being hybridized proximate to the 5' terminus of the second downstream probe;

wherein the 5' end of at least one of the first or second downstream probes is modified to be ligation incompetent absent correction.

Another aspect of the invention provides kits containing the above modified probes which can be used for target nucleic acid detection and/or amplification with reduced or no target independent amplification. Such kits comprise in one or more suitable containers:

(a) a set of oligonucleotides comprising an upstream probe and a downstream probe, both probes having sequences substantially complementary to portions of a target nucleic acid sequence, the 3' terminus of the first upstream probe hybridizing proximate to the 5' terminus of the first downstream probe, wherein the 5' end of said downstream probe is modified to be ligation incompetent absent correction;

(b) one or more correcting reagents for correcting the ligation incompetent downstream probe in a target-dependent manner to render the downstream probe ligatable and for rendering the upstream and downstream probes ligation competent; and (c) a ligating reagent for ligating the corrected downstream probe to the upstream probe.

The correcting reagents may include one agent for cleaving in the case of overlapping probes; or it may include reagents for cleaving and extending. If two functions are needed for correction, two distinct reagents may be used, but it is preferable to employ a polymerase having both polymerization and 5' to 3' exonucleolytic activities. Preferably the polymerase is thermostable if it will be used for amplification methods.

BRIEF DESCRIPTION OF THE DRAWINGS

The figures generally depict various preferred embodiments according to the invention. In each figure, frame a shows the two sets of probes, including a preferred modification on the 5' end of the downstream probes; frame b shows the first set of probes hybridized to a strand of target DNA; and frame c shows the first two probes after correction of the modified probe but before ligation of probe 1 to probe 2. Although frame a depicts modifications in both downstream probes, the invention requires only that one downstream probe be modified. In each figure, the shaded rectangle represents one label or reporter group, typically a first hapten; while the shaded oval represents a second label or reporter group which may or may not be a second hapten.

FIG. 1 is a schematic example of a nucleic acid amplification technique using two sets of blunt ended probes wherein the downstream probes have 5' hydroxyl termini in place of the 5' phosphate required for ligation competency.

FIG. 2 is a schematic example of a nucleic acid amplification technique using two sets of blunt ended probes wherein each downstream probe has a 5' hydroxyl terminus and a one base terminal mismatch with respect to complementary probe and target. Ligation incompetency is provided not only by the 5' hydroxyl termini, but also by weakened hydrogen bonding to template because of the mismatched terminal base.

FIG. 4 is a schematic example of a nucleic acid amplification technique using two sets of non-blunt ended probes which have downstream probes with 5' extensions. These 5' extensions are not hybridizable to each other or to their respective targets. These downstream probes also have 5' hydroxyl termini as shown. Ligation incompetency is provided by steric constraints imposed by the extensions and by the 5' hydroxyl.

FIG. 5 is a schematic example of a nucleic acid amplification technique using two sets of non-blunt ended probes wherein each downstream probe has a one base 5' extension, and the extensions are complementary to each other but not to the target. The downstream probes also have 5' hydroxyl termini as shown. Ligation incompetency on target is provided by weakened hydrogen bonding due to the terminal mismatch and by the 5' hydroxyl.

FIG. 6 is a schematic example of a nucleic acid amplification technique using two sets of blunt ended probes wherein the downstream probes each have a 5' hydroxyl terminus, and the 5' terminal base mismatches the complementary probe and the target. Ligation incompetency is provided by weakened hydrogen bonding due to the terminal mismatches and by the 5' hydroxyl.

FIG. 7 is a schematic example of a nucleic acid amplification technique using two sets of non-blunt ended probes with 3' extensions (in the upstream probes) which match each other and the target. The downstream probes have 5' hydroxyl termini. Ligation incompetency is provided by the 5' hydroxyl.

DETAILED DESCRIPTION

Figure 3A:
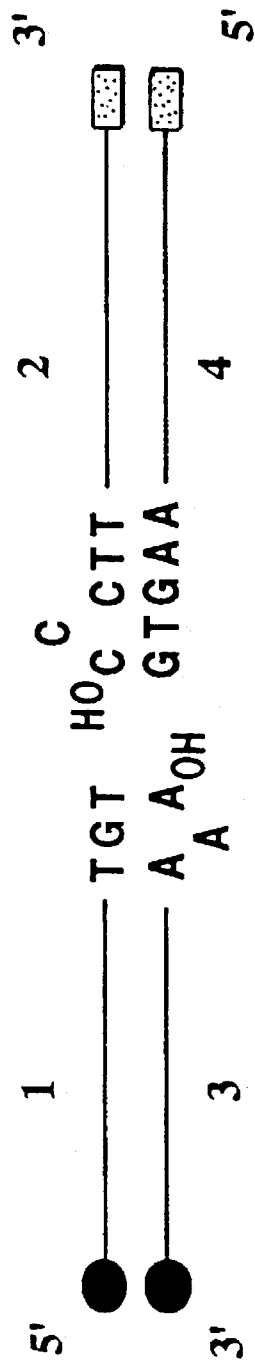
FIG. 3 is a schematic example of a nucleic acid amplification technique using two sets of blunt ended probes wherein each downstream probe has a 5' hydroxyl terminus and a one base internal mismatch with respect to its complementary probe and target. As in FIG. 2, target independent ligation is reduced by both the 5' hydroxyl and the weakened hydrogen bonding due to the internal mismatch.

The invention will now be described in detail in accordance with the following general outline:

I. Definitions
II. Ligation Incompetent Modifications and Correction Thereof
  A. Non-phosphorylated 5' termini
  B. Mismatched bases, terminal and internal
III. Probe Configurations
  A. Blunt
  B. Non-blunt
IV. Methods of Use
  A. Detection Methods
  B. Amplification Methods
  C. Polymerization Independent Methods
V. Modes of Detection
  A. Ligated Complex
  B. Released Fragments
VI. Compositions and Kits
VII. Examples
VIII. Sequence Listing I. Definitions As used in this application, the following terms have the meanings indicated.

"Target" or "target sequence" refers to the nucleic acid whose presence or absence is sought to be detected or differentiated from other nucleic acid, whose sequence may be very closely related. The target nucleic acid comprises deoxyribonucleic acid (DNA) or, less typically, ribonucleic acid (RNA). For the purpose of this invention, the target is described to be single stranded. However, this should be understood to include the case where the target is actually double stranded but is simply separated from its complementary strand (also referred to as "target complement") prior to hybridization with the probes. In the case of a double stranded target, the second set of probes can also be used in the initial step to hybridize to the target complement. In the case of a single stranded target, the second set of probes would not participate in the initial hybridization step, but would participate in subsequent hybridization steps, for example, by hybridizing to the ligated product.

"Probes" refer to the oligonucleotide segments utilized in the invention. They are from 10 to about 100 nucleotides long, preferably from about 15–35, and have a defined base sequence suitable for the desired target. Probes are usually DNA, but may be RNA or of mixed DNA/RNA composition. Certain probes are modified at their 5' end, as described herein. Probes may be from natural or synthetic sources.

"Bases" shall refer to the pyrimidine and purine compounds Guanine (G), Cytosine (C), Adenine (A) and Thymine (T) in the case of DNA; and, in the case of RNA, the Uracil (U) replaces Thymine. "Bases" also includes analogs, derivatives and modified base, such as those recognized in 37 CFR §1.822(p)(1), which are capable of hybridizing to the target under assay conditions. Unless context dictates otherwise, "base" is sometimes also used to refer to the complete nucleotide residue, including the sugar and phosphate moieties, such as when speaking of filling in the gap with the appropriate bases.

Bases are known to pair together in cannonical fashion: A with T and C with G in DNA, and, in the case of RNA, A with U and C with G. With respect to individual bases, "complementary" denotes the pairing or "matching" in accordance with the above description. Thus, A paired with G or C represents "mismatched" or "non-complementary" bases. With respect to oligonucleotide probes, however, a probe that is "complementary" to another probe or to target means the oligonucleotide can hybridize with the complementary probe or target tinder hybridization conditions. Thus, complementary probes may include sequences that may have mismatched base pairs in the hybridizable region, provided the sequences can be made to hybridize under hybridization conditions. Preferably, the probes are sufficiently complementary to hybridize selectively to their targets or complementary probes.

A "stopbase" refers to the nucleotide at which a nucleolytic or polymerization process terminates. For example, a stopbase may exist as a template base for which the complementary base is absent from the dNTP pool. Alternatively, a stopbase may exist as a nuclease resistant linkage in a downstream probe. Alternative stopbases can be used in combination as well.

"Assay Conditions" refers to the conditions of LCR with regard to temperature, ionic strength, probe concentration and the like. These are generally known in the art. LCR involves essentially two states or conditions: annealing or hybridization conditions, and denaturation conditions.

"Hybridization conditions" is defined generally as conditions which promote nucleation and annealing. It is well known in the art, however, that such annealing and hybridization is dependent in a rather predictable manner on several parameters, including temperature, ionic strength, probe length and G:C content of the probes. For example, lowering the temperature of the reaction promotes annealing. For any given set of probes, melt temperature, or Tm, can be estimated by any of several known methods. Typically hybridization conditions include temperatures which are slightly below the melt temperature. Ionic strength or "salt" concentration also impacts the melt temperature, since small cations tend to stabilize the formation of duplexes by shielding the negative charge on the phosphodiester backbone. Typical salt concentrations depend on the nature and valency of the cation but are readily understood by those skilled in the art. Similarly, high G:C content and increased probe length are also known to stabilize duplex formation because G:C pairings involve 3 hydrogen bonds where A:T pairs have just two, and because longer probes have more hydrogen bonds holding the strands together. Thus a high G:C content and longer probe lengths impact the "hybridization conditions" by elevating the melt temperature. Once probes are selected, the G:C content and length will be known and can be accounted for in determining precisely what "hybridization conditions" will encompass. Since ionic strength is typically optimized for enzymatic activity, the only parameter left to vary is the temperature and obtaining suitable "hybridization conditions" for a particular probe set and system is well within ordinary skill.

"Denaturation conditions" is defined generally as conditions which promote dissociation of double stranded nucleic acid to the single stranded form. These conditions include high temperature and/or low ionic strength; essentially the opposite of the parameters described above as is well understood in the art.

"Ligation" is a general term which includes any method of covalently attaching two probes. The preferred method is enzymatic ligation. For purposes of this application, "ligation competent" refers to probe ends that are capable of being ligated by enzymatic ligase. For known enzymatic ligases, ligation competency requires nucleic acid segments such that a 3' hydroxyl terminus is disposed adjacent to a 5' phosphorylated terminus. Conversely, "ligation incompetent" probes do not present ends suitable for ligation, typically because of lack of 3' hydroxyl, lack of 5' phosphate or lack of adjacency. Many examples of ligation incompetency are discussed later. Ligation incompetency is a temporary state in this invention, exisiting only until "correction". Thus it is sometimes referred to as "ligation incompetent absent correction."

"Correction" refers to repair of the modification that rendered the probe ligation incompetent in the first place. Specific correction mechanisms are discussed later in connection with specific modifications, but relate generally to one or more of: 1) creating or restoring a 3' hydroxyl; 2) creating or restoring a 5' phosphate: or creating adjacency, either by cleaving an overhanging extension or by filling in a gap. It is an important feature of the present invention that correction be "target-dependent", i.e. that it take place substantially only in the presence of target or target equivalent, and not in the presence of the other probes. "Template dependent" is the same as "target dependent" in that the template is ligated probe product only, and not unligated probes. Preferably, a hybridized probe is corrected enzymatically by an agent having a suitable exonucleolytic activity which is dependent upon the sequence information contained within the target.

"Nucleolytic activity" refers to the activity, preferably of an enzyme, which excises or degrades a DNA or RNA substrate. Nucleolytic activity may be exonucleolytic (from an end inward) or endonucleolytic (from within). For purposes of this invention the type of nucleolytic activity is not important, provided it is able to correct the modified 5' end in a target dependent fashion. For simplicity, nucleolytic activity described herein is generally referred to as "exonucleolytic" activity, but this is not intended to limit the nucleolytic activity to any particular mechanism. Thus, as used herein the terms "exonucleolytic" or "exonuclease" include nucleic acid degradation whether from the end or from within, whether monomer or larger fragments are the degradation product, and whether by enzymatic or chemical means.

Suitable exonucleolytic activity may be found in an exonuclease enzyme, or in the 5'–3' exonuclease activity traditionally associated with some DNA polymerases. For example, a DNA polymerase with DNA synthesis dependent, strand replacement 5' to 3' exonuclease activity as well as a 5' to 3' polymerization activity has been described in Gelfand, D., *Taq DNA Polymerase* in PCR Technology: Principles and Applications for DNA Amplification, Erlich, H. A., Ed., Stockton Press, N.Y. (1989) Chapter 2). A similar activity has been demonstrated in the thermostable DNA polymerase of Thermus origin, commercially available from Molecular Biology Resourses (MBR) Milwaukee, Wis. In the presence of the appropriate dNTP(s), these DNA polymerases will initiate synthesis from the 3' hydroxyl terminus of a probe hybridized to a target DNA, proceed along the DNA target template, degrading downstream hybridized DNA sequences and replacing them in the process.

For convenience herein, probes are referred to as "upstream" or "downstream". When two probes hybridize to distinct regions of the same linear nucleic acid, and the 3' terminus of one probe points towards the 5' terminus of the other, the former is called the "upstream" probe and the latter is called the "downstream" downstream probe, regardless whether the strand(s) posesses a "sense" direction for coding purposes. These two oligonucleotide probes are collectively referred to as a set of probes or oligonucleotides or a "ligatable pair" (as distinct from a complementary pair). In frame a of each figure, two such sets of probes are shown.

The first set consists of Probes 1 (also referred to as "first upstream probe") and 2 ("first downstream probe"). The second set consists of Probes 4 ("second upstream probe") and 3 ("second downstream probe"). Depending on context, a set of probes can also refer to all four probes, or to two probes which hybridize to opposite strands.

A distinction is drawn herein between the "end" of a probe and its "terminus". A 3' or 5" "terminus" refers to the nucleoside carbon designated 3' or 5' respectively, and thus refers to the terminal point of an oligonucleotide. By contrast, a 3' or 5' "end" refers more generally to the region near the 3' or 5' terminus, respectively. The "end" will include the "terminus" but will also include several adjacent bases, up to one-quarter or one-third of the entire oligonucleotide. The term "blunt-ended" refers, however, to coterminal probes as defined later.

When a set of upstream and downstream probes hybridize to their target, they lie "proximate" each other. The term "proximate" means the termini are within about 20 nucleotides apart and includes the situations in which: (1) the 3' terminus of one probe abuts the 5' terminus of the other probe, i.e. the probes are directly adjacent; (2) there is a "gap" formed by missing base(s) between the 3' terminus of one hybridized upstream probe and the 5' terminus of the hybridized downstream probe; and (3) the 5' end of the downstream probe is not complementary or only partially complementary to a limited region of the target, whereas the 3' end of the upstream probe is complementary to the same region. When two such probes hybridize to the target, an "overlap" is formed at the 5' end of the downstream probe at this limited region, as is shown in FIG. 4b.

The term "WRTP" is an abbreviation for "with respect to probes" which is used in describing a mismatch (terminal or internal mismatch) between two hybridizable probes. In the case of blunt ended probes, the mismatch may occur between Probes 1 and 3; and/or between Probes 2 and 4. In addition, non-blunt ended probes have other regions for potential mismatches. In 5' extension non-blunt ended probes, the mismatch may occur between the 5' extensions of Probes 2 and 3. In 3' extension non-blunt ended probes, the mismatch may occur between the 3' extensions of Probes 1 and 4.

The term "WRTT" is an abbreviation for "with respect to target" which is used in describing a mismatch (terminal or internal mismatch) between a probe and its target. Probes may be designed to include one or more mismatches WRTT and WRTP, or they may include mismatches WRTT but not WRTP.

As used herein, "label" refers to any moiety capable of signalling or reporting the presence of a probe to which it is attached. The label may be direct, such as with chemiluminescent compounds, fluorescent compounds or radioactive isotopes, or it may be indirect, such as with biotin or another ligand or hapten. In the case of indirect labels, a further reaction is utilized to realize measurable signal. The further reaction may include reaction with a conjugate label containing a specific binding partner for the hapten and a suitable direct label. Exemplary radioisotopes include $^{32}$P and tritium; fluorescein, FITC, rhodamine and Texas Red are fluorescent labels; acridine and quinoline are examples of chemiluminescent labels. Some illustrative haptens include many drugs (eg. digoxin, theophylline, phencyclidine (PCP), salicylate, etc.), T3, biotin, fluorescein (FITC), dansyl, 2,4-dinitrophenol (DNP); and modified nucleotides such as bromouracil and bases modified by incorporation of a N-acetyl-7-iodo-2-fluorenylamino (AIF) group; as well as many others. Many other examples of each type of label are known to those skilled in the art.

Carbazole and Adamantane derived haptens are discussed in the examples. These are described in co-pending U.S. patent application Ser. No. 808,508, filed Dec. 17, 1991, entitled "Haptens, Tracers, Immunogens and Antibodies for 3-phenyl-1-adamantaneacetic Acids"; and in co-pending U.S. patent application Ser. No. 808,839, filed Dec. 17, 1991, entitled "Haptens, Tracers, Immunogens and Antibodies for Carbazole and Dibenzofuran Derivatives." Methods for adding a hapten label to an oligonucleotide through the use of a phosphoramidite reagent are described in Thuong, N. T. et al., *Tel. Letters*, 29(46):5905–5908 (1988), or Cohen, J. S. et al., U.S. patent application Ser. No. 07/246,688 (NTIS order no. Pat-Appl-7-246,688 (1988).

II. Ligation Incompetent Modifications and Correction Thereof

This invention involves downstream probes with 5' ends that are ligation incompetent absent correction. As mentioned, correction can be the removal, replacement, or further modification of this end to render it ligatable, and may simultaneously involve changes to the upstream probe as well.

A. Non-phosphorylated 5' termini

A first form of ligation incompetent ends is a non-phosphorylated 5' terminus, which cannot be ligated to a 3' hydroxyl terminus of the upstream probe but which can be corrected in a target dependent manner to render it ligatable (hereinafter referred to as "non-phosphorylated 5' terminus", "non-phosphorylated 5' terminus", or described as "non-phosphorylated" in relation to the 5' terminus of the downstream probe). While the ligation incompetent probe is hybridized to target, the 5' terminus is "corrected" by removal of the non-phosphate groups and replacement with or exposure of a phosphate group. Typically this is effected by removal the entire nucleotide bearing the 5' non-phosphate group, using an agent having exonucleolytic activity which leaves a 5' phosphate terminus exposed on the next adjacent nucleotide.

The removed nucleotide is typically replaced by adding to the 3' terminus of the upstream probe a comparable nucleotide. Thus, a DNA polymerase with 5' to 3' exonucleolytic activity is an ideal correcting agent since both of the necessary activities are manifested in one enzyme. This process of correction by cleaving from a 5' end of a downstream probe and replacing on a 3' end of the corresponding upstream probe resembles a "nick translation" reaction although a labeled replacement nucleotide is not required. In essence, a "nick" between ligation incompetent probes is translated downstream one or more bases and, in doing so, a ligation incompetent end is corrected to become ligation competent. Not all embodiments, however, start out as simple "nicks".

The 5' non-phosyphorylated end means simply that no phosphate is attached to the 5' terminus of a nucleic acid chain via the exocyclic (5') carbon. Instead, the 5' carbon may connect to H, OH or any other chemical group which is incapable of serving as a substrate for ligation, but does not observably hinder the correcting activity of polymerase or exonuclease in removing the nucleotide containing the "non-phosphate" group from the hybridized downstream probe and/or in extending the hybridized upstream probe. Thus, the non-phosphate group should have a molecular weight of at least one but less than a molecular weight that would give rise to a tertiary structure that would prevent correction of the hybridized probes. It may include phosphate derivatives with the mentioned characteristics. The non-phosphate group may be attached directly or via a linker to the 5' terminus of the downstream probe, or it can be the linker alone. It may also include part of a labeling or reporting system as is described later. The non-phosphate group includes but is not limited to the following groups: chromophores, haptens, radiolabeled compounds, peptides, magnetic particles, carbohydrates, and amino-bearing groups such as Aminomodifier. Other examples of the non-phosphate group are: -hydryl; -hydroxyl; -sulfhydryl (thiols); hydrocarbons including -methyl; -acyl; -halides, -primary amines; -nitro; and -cyclic compounds. Linkers that can be used include: alkenes, alkynes, amides, amines, esters, ethers, ketones, sulfides, sulfones, sulfoxides, and imines. The 5' non-phosphorylated end is preferably a hydroxyl, a methyl, or an Aminomodified terminus, or an end containing a fluorescent label or a component of a fluorescent labeling system.

B. Mismatched Bases

A second type of ligation incompetent 5' end is a terminal or internal mismatch WRTT and WRTP within the downstream probe. A "terminal" mismatch occurs in the very last residue of the probe, while an "internal" mismatch need only occur near the end, typically within 1 to about 5–8 bases from the 5' terminus. Either type of mismatch may consist of from 1 to about 5, more preferably 1 or 2 bases long, typically all adjacent one another. It has been found that probes having such a mismatch are not ligated as efficiently as ligation competent probes, especially in a preferred embodiment where the 5' end also includes a non-phosphorylated terminus. Presumably, terminal or internal mismatches create a "loose" 5' end due to reduced hydrogen bonding which is a suitable substrate for the exonuclease activity.

An example of a terminal mismatch is shown in FIG. 2, wherein two sets of blunt ended probes are shown, the downstream probes each having a 5' hydroxyl terminus and a one base terminal mismatch with respect to its complementary probe and its target. In the presence of a polymerase, a ligase, and a dNTP pool containing 2'-deoxythymidine 5'-triphosphate (dTTP), correction occurs by removing from the downstream probe the mismatched G having the ligation incompetent 5' hydroxyl terminus and by extending the upstream probe with dTTP until the probes abut each other and can be ligated. The polymerase will continue to extend the upstream probe and degrade the downstream probe until it reaches a downstream stopbase, in this case, the G in the target. Having degraded and removed the 5' hydroxyl terminus of the downstream probe, the polymerase exposes the C in the downstream probe which has a 5' phosphate terminus, indicated by "p", which is ligation competent. The "TT" shows the thymidylate residues from the dTTP that are used to extend the upstream probe. With the two probes abutting each other and the downstream probe having been corrected to contain a 5' phosphate terminus, the two probes can then be ligated.

Under the present assay conditions, it appears that in order to have efficient LCR amplification involving polymerization, the correction of a mismatched base requires the replacement of at least one hybridized nucleotide immediately downstream from the mismatched base. Thus, for efficient amplification to occur, the dNTP pool should also contain the base that is required for this replacement. This is illustrated in FIG. 6, in which both dATP and dCTP should be available for efficient amplification to occur.

Figure 3B:
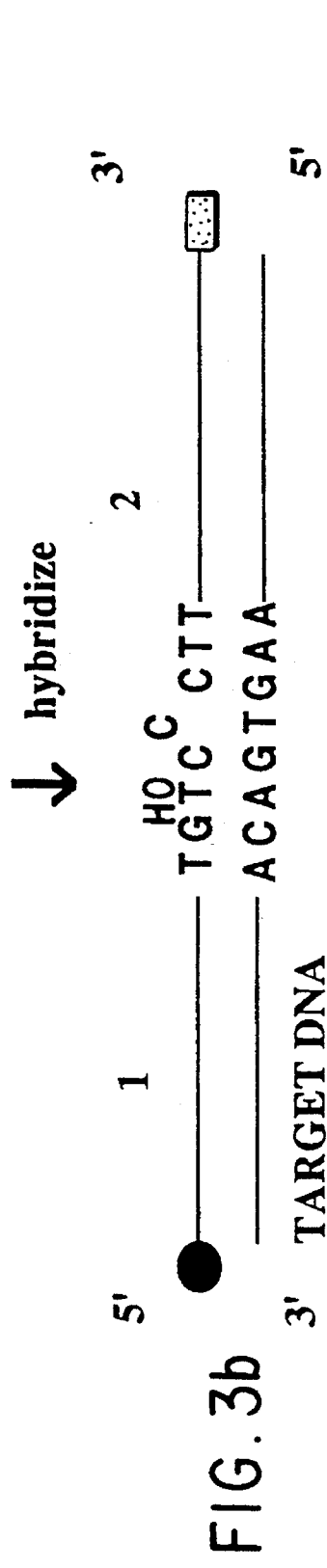
Figure 3C:
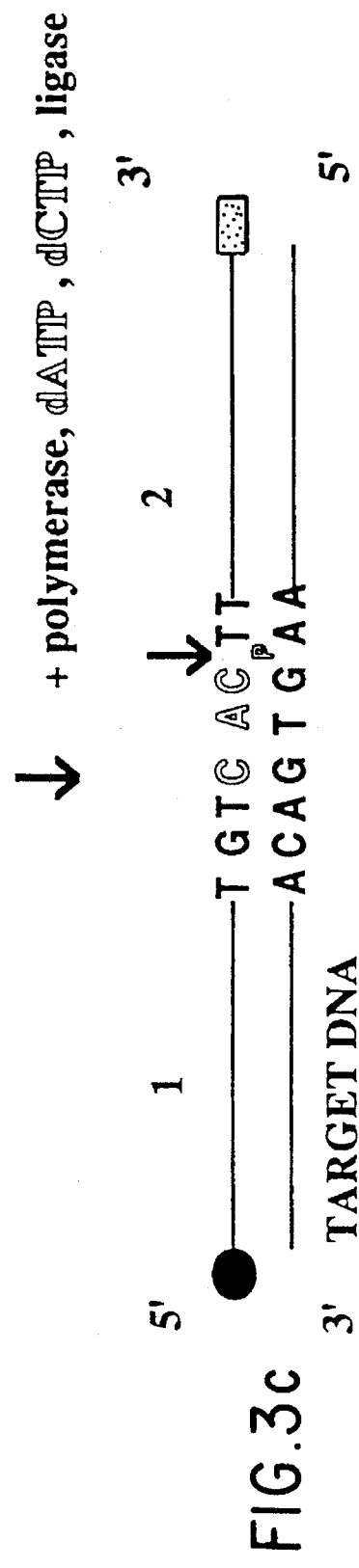

An example of an internal mismatch is shown in FIG. 3. In this figure each downstream probe each has a 5' hydroxyl terminus and a one base internal mismatch with respect to its complementary probe and target. In probe 2 the second C fails to complement the T in probe 4 and the target. Similarly, the second A of probe 3 fails to complement the G in probe 1 and target. These internal mismatches, combined with the 5' hydroxyl termini, provide ligation incompetent probes. Correction occurs in the presence of a polymerase, a ligase, and a dNTP pool containing 2'-deoxyadenosine 5'-triphosphate and 2'-deoxycytidine 5'-triphosphate (dCTP). The same mechanism as shown in FIG. 2 occurs here. Once the probes in a probe set have hybridized to their target, the polymerase removes the 5' hydroxyl terminus from the downstream probe, the internal mismatch, and a hybridized base immediately downstream from the mismatched base to expose a 5' phosphorylated terminus, while extending the upstream probe to abut the corrected downstream probe such as to allow ligation of the upstream probe to the downstream probe. In FIG. 3, three C's are removed from the 5' end of probe 2 and three A's are removed from probe 3. Virtually simultaneously, probe 1 is extended by the addition of CAC. Probe 4 is also extended by the addition of ACA. In probe 4 the A serves as a stopbase for extension of probe 1. While not shown, either A or C could serve as stopbase in probe 1.

If a target dependent 5' to 3' exonuclease or a polymerase with 5' to 3' target dependent exonuclease activity is used, the 3' end of an upstream probe must not include a mismatch WRTT or correction does not occur efficiently. However, the 3' end of the upstream probe can mismatch WRTP. But because of the antiparallel nature of DNA binding, the probe with which the 3' upstream probe mismatched is in reality the 5' end of a downstream probe of the other probe set. Therefore, this mismatch is viewed as the same as a 5' mismatch of the downstream probe.

A subset of mismatched ligation incompetent ends is when the probes of a ligatable pair are overlapping. In this case, the 5' end of the downstream probe needs to occupy the same position on the target as the 3' end of the upstream probe. But since the 5' end is mismatched, it is displaced by the upstream probe and the 5' end dissociates or becomes "loose" from the target, which is a suitable substrate for exonucleolytic acitivity. Overlaps, being defined with regard to the ligatable partner of each probe set, should not be confused with extensions (see below), which are defined with regard to the complementary probe.

An overlapping embodiment is shown in FIG. 4 and is discussed below.

The probes are preferably designed so that the termini that are not intended for ligation ("outside termini") cannot be ligated, and this ligation incompetency cannot be corrected. An example of these undesirable ligations is the ligation of the 5' terminus of the upstream probe to the 3' terminus of the downstream probe. The outside terminus of at least one of the probes can be blocked with a "hook" or marker which includes hapten, biotin, and fluorescein. In the Examples below, the hooks or markers are adamantane derived hapten, carbazole derived hapten, biotin derived hapten, and fluorescein derived hapten. The carbazole derived hapten and adamantane derived hapten are shown as darkened round circles and shadowed squares, respectively, at the outside termini of the probes in FIGS. 1 to 4; and 6 to 7. In FIG. 5, these blocking groups are fluorescein and biotin. These blocking groups can serve a dual purpose by also acting as a label for subsequent detection or capture of the probes. Further description is found in the Examples below.

III. Probe Configurations

Although several means for creating ligation incompetent modified ends have been described, it should be apparent that there are further variations possible with regard to probe configuration. Thus, ends which are ligation incompetent may be found in several probe configurations, including blunt ended and non-blunt ended probes, as discussed below.

A. Blunt End Configurations

"Blunt ended probes" describes probes which are co-terminal at their ends that are intended for ligation. That is, the 3' end of Probe 1 is co-terminal with the 5' end of Probe 3; and/or the 5' end of Probe 2 is co-terminal with the 3' end of Probe 4. FIGS. 1 to 3, and 6 show examples of blunt ended probes. While it should be realized that probes on one side (e.g. probes 1 and 3) may be blunt while probes on the other side are not, FIG. 1 and the following description assume blunt ended probes on both sides.

FIG. 1 shows two sets of blunt ended probes wherein the downstream probes (2 and 3) have 5' non-phosphate modified termini in the form of hydroxyl groups. Frame 1a shows the two sets of probes such that the first set of probes are complementary to the second set, and the complementary probes are lined up accordingly in FIG. 1a. For simplicity, frame 1b only shows the first set of probes hybridized to its target DNA sequence. The bases of these probes are complementary to their respective targets. As shown in the arrow from Frame 1b to 1c, the correction is carried out in the presence of a polymerase, a ligase, and a deoxyribonucleoside 5'-triphosphate (dNTP) pool containing 2'-deoxythymidine 5'-triphosphate (dTTP). Using the information contained in the target template, the polymerase removes the ligation incompetent hydroxyl end in the downstream probe (2) and extends the upstream probe (1) so the upstream and downstream probes abut each other and can be ligated. The polymerase will potentially continue to extend the upstream probe and degrade the downstream probe until it reaches a downstream stopbase. In this case, this corresponds to the G in the target. Having degraded and removed the 5' hydroxyl end of the downstream probe, the polymerase exposes the C in the downstream probe which has a 5' phosphate terminus, indicated by "p", which is ligation competent. The "TT" shows the thymidylate residues from the dTTP that are used to extend the upstream probe. With the two probes abutting each other and the downstream probe having been corrected to contain a 5' phosphate terminus, the two probes can then be ligated. The point of ligation is shown with an arrow in frame 1c.

In the simplest case of blunt ends with no mismatches, the 5' terminus of the downstream probes must be non-phosphorylated. Otherwise, a 5' non-phosphorylated terminus is not required, though it is preferred as discussed above in connection with the preferred embodiments of FIGS. 2 and 3. In blunt probe configurations with terminal or internal mismatches, a mismatch WRTT in the downstream probes by necessity dictates a mismatch WRTP, but this is the only situation where this is necessarily true. As before, the number of mismatched bases at the 5' end can be between 1 to 5, and most preferably 1 or 2.

The currently preferred variation of blunt ended probes is a downstream probe with a 5' non-phosphorylated terminus and terminal or internal mismatch WRTP and WRTT as shown in FIGS. 2 and 3.

B. Non-Blunt Configurations

The present invention also encompasses non-blunt ended probes. Here, at least one upstream probes is not co-terminal with its complementary downstream probe. There are two possibilities: (1) 3' extensions (in the upstream probe) and (2) 5' extensions (in the downstream probe). Note that "extensions" are defined with reference to a probe's complement rather than its ligation partner and that they need not be the same type or length on opposite sides. Where two sets of probes are used, and both sets possess the same type (i.e. either 5' or 3') of extensions, then the extensions may be hybridizable (thus forming sticky-ends) or non-hybridizable (non-sticky ends) to each other. If the extensions are not hybridizable to each other, the extensions are preferably between one to about ten bases, more preferably between 1 to about 5 bases, and most preferably one or two bases in length. If the extensions are hybridizable to each other, the extensions are preferably shorter; e.g. from one to about four bases, preferably only one or two bases in length. Where the probes have 3' or 5' extensions, if they are hybridizable it is preferred that the downstream probes have non-phosphorylated 5' termini in addition to any other mode of ligation incompetency.

(1) 3' Extensions

With 3' extensions, the first and second downstream probes may also have 5' terminal or internal mismatch bases with regard to their respective complementary probes. Where a 5' to 3' polymerase is used, bases in the 3' extensions should be complementary to the target; whereas all or some of the bases in the 5' extensions may be either complementary or non-complementary to the target.

An example of probes with hybridizable 3' extensions is shown in FIG. 7. As shown in FIG. 7a, the extensions are: a "T" on probe 1 and an "A" on probe 4. Since "A" is complementary to "T", the extensions are hybridizable to each other, and probes could be ligated independently of target unless the 5' end is non-phosphorylated. Correction is carded out in the presence of a polymerase, a ligase, and a dNTP pool containing 2'-deoxythymidine 5'-triphosphate (dTTP) and 2'-deoxyguanosine 5'-triphosphate (dGTP). The polymerase removes the 5' hydroxyl end of the downstream probe to reveal an available 5' phosphate, "p", while extending the upstream probe to abut the corrected downstream probe such as to allow the ligation of the two probes.

In another embodiment, that of 3' non-hybridizable extensions (not shown), the 3' extensions are not hybridizable to each other. The extensions can be rendered non-hybridizable to each other by having a sufficient number of bases that are not complementary between them. Since 3' ends should be hybridizable with target to accomodate the preferred polymerase agent, making these extensions non-hybridizable to each other means that there will necessarily be a gap between the proximate hybridized probes. If gaps are involved they can be between 1 to 20 bases long; practically, however, much shorter gaps are preferred, for example from 1 to 3 or 5 bases. The targets, probes and dNTP reagents should be selected such that this gap can be filled along with the replacement of any "corrected" bases from the 5' end of the modified downstream probe.

(2) 5' Extensions

An example of non-blunt probes with 5' hybridizable extensions is shown in FIG. 5. As shown in frame 5a, the extensions are "A" on probe 2 and "T" on probe 3. In this case, the extensions are hybridizable to each other, since "A" is complementary to "T", but neither is complementary to the G:C pair in the target. The downstream probes 2 and 3 also have 5' hydroxyl termini. Correction involves a polymerase, a ligase, and a dNTP pool containing 2'-deoxycytidine 5'-triphosphate (dCTP) and 2'-deoxyguanosine 5'-triphosphate (dGTP). The polymerase removes each 5' hydroxyl terminus along with the base which mismatches the target and the matching base immediately downstream from the mismatched terminal base. The polymerase also extends the upstream probes 1 and 4 with dCTP and dGTP, respectively, to create the ligation competent ends.

In another embodiment, that of 5' non-hybridizable extensions, the extensions are not hybridizable to each other. For all the probe pairs with 5' extensions, if a 5' to 3' DNA polymerase and a deoxyribonucleoside 5'-triphosphate (dNTP) pool are used in the reaction mixture, it is preferable that the 5' extension not be complementary to the target. If it is, the dNTP pool needed for correction will include the bases which are complementary to the extensions and the DNA polymerase can "end polish" the upstream probe independently of target. "End polishing" can occur with 5' extensions, using the extension as a template for polymerase to extend the complementary upstream probe. End polishing is not fatal to the invention, but it can reduce the case of 5' extensions to a case of blunt end probes. Thus, in the case where a downstream probe with a 5' extension is used, the 5' end of this probe should have one or more of the following features: (1) a non-phosphorylated terminus; (2) if another set of probes also contains a downstream probe with a 5' extension, both these extensions are not hybridizable to each other under a specific assay condition; and (3) non complementary bases WRTT.

Using FIG. 4 as an example, the 5' extensions shown (GGG) are hybridizable with neither each other nor target. Frame 4b shows what will happen when probes 1 and 2 hybridize with the target. Because the 5' extension mismatches the target, it dissociates and becomes "loose", establishing a good substrate for exonucleolytic activity. Correction utilizes polymerase, dTTP and ligase. The exonucleolytic activity cleaves the three G residues and at least one T residue to reveal a 5' phosphate group. The polymerase adds at least one T residue to the 3' terminus of probe 1 (two are shown added), but stops at the template G since dCTP is not provided. Ligation occurs at the arrow of frame 4b.

Though in the figures the complementary probe pairs (Probes 1 and 3; and Probes 2 and 4) exhibit the same formats of modified probes; the two probe pairs may differ. For example, Probes 1 and 3 can be of one format of blunt ended probes, whereas Probes 3 and 4 can be of a different format of blunt ended probes or a format of non-blunt ended probes, and vice versa. The variations are limited, for example, by the need to accommodate a dNTP pool which omits one or more types of bases in order to provide for a "stopbase" and/or to avoid end polishing, as discussed above.

IV. Methods Using 5' to 3' Exonuclease/Polymerase Activity

One aspect of the present invention uses a DNA polymerase with DNA synthesis dependent, strand replacement 5' to 3' exonuclease activity as well as a 5' to 3' polymerization activity (Gelfand, D., *Taq DNA Polymerase* in PCR Technology: Principles and Applications for DNA Amplification, Erlich, H. A., Ed., Stockton Press, N.Y. (1989) Chapter 2). Taq DNA polymerase has been shown to exhibit this activity, and a similar activity has been demonstrated in the thermostable DNA polymerase of Thermus origin, commercially available from Molecular Biology Resourses (MBR) Milwaukee, Wis. In the presence of the appropriate dNTP(s), these DNA polymerases will initiate synthesis from the 3' hydroxyl terminus of a probe hybridized to a target DNA, proceed along the DNA target template, degrading downstream hybridized DNA sequences and replacing them in the process. In the present invention the downstream DNA is the downstream probe.

A. Detection Methods

The methods of the invention can be used as simple detection of target nucleic acid or as an amplification technique. For detection only two probes (one set), the downstream one being modified at its 5' end, need to be employed. In the presence of target the modification is corrected as described above and the probes are ligated. The ligation event can be monitored as a measure of the presence of target by any of the methods disclosed. The detection technique is analogous to those disclosed, for example, in EP 185 494 and EP 246 864 but have the improvement of reduced target independent ligation. The hybridization, correction and ligation steps are identical to those discussed below in connection with Amplification Methods, but need be performed on only one set of probes. No cycling is necessary.

B. Amplification Methods

However, the invention is best adapted for use in a method that includes amplification of the target sequence, such as the ligase chain reaction (LCR). Amplification provides improved sensitivity and permits detection of much lower levels of target DNA. Linear amplification is achievable by cycling with just one probe set, whereas exponential amplification utilizes two probe sets, one complementary to the other. As applied to LCR, a downstream probe containing a 5' end which is ligation incompetent absent correction is used. This modification prevents the target independent ligation of the probes. Additionally, in the presence of a target nucleic acid sequence, proximate LCR probes hybridize but are not ligatable. Sequence information contained within the target DNA is used as a template for correction of the ligation incompetent end. A DNA polymerase with synthesis dependent, strand replacement 5' to 3' exonuclease activity may be used to extend the upstream probe and hydrolyze the downstream probe using the target nucleic acid as a template. By using a subset of four dNTPs required for DNA synthesis, the extension of an upstream probe (and therefore the hydrolysis of a downstream probe) could be controlled such that when a template base in the target is encountered to which no complementary dNTP is present, synthesis (and hydrolysis) terminate. The resultant downstream probe possesses a 5' phosphate which is adjacent to the 3' hydroxyl terminus of the extended upstream probe. Adjacent probes thus present a suitable substrate for ligation by DNA ligase.

In a subsequent step the ligated probes are separated and become a "target" for a second set of probes complementary to the first set. The second set preferably also takes advantage of the modified probes according to the invention. The process of hybridization, (optional correction) and ligation are repeated for the second probe set.

In general, the preferred amplification method comprises repeated steps of (a) hybridizing the ligation incompetent modified probes to the target; (b) correcting the modification in a target dependent manner to render the probes ligatable; (c) ligating the corrected probe to its partner to form a fused or ligated product; and (d) dissociating the fused product from the target and repeating the hybridization, correction and ligation steps a number of times for each probe set to amplify the desired target sequence. Where the target is double-stranded, the above steps will also apply to the target complement, using Probes 3 and 4 of the second set. But, even absent a double-stranded target, Probes 3 and 4 are preferably used to amplify and/or detect the ligated Probes 1 and 2. Similarly, the ligated Probes 3 and 4 serve as the target for Probes 1 and 2 for further detection. Thus, amplification of the target sequence can be achieved by using an excess of Probes 1, 2, 3, and 4, and assay conditions that include cycling.

1. Hybridization of Probes to the Targets

The hybridization of probes to their targets (and optionally to the target complements) is adequately explained in the prior art; e.g. EP-320,308 and EP-439,182. Probe length, probe concentration and stringency of conditions all affect the degree and rate at which hybridization will occur. Preferably, the probes are sufficiently long to provide the desired specificity; i.e, to avoid being hybridizable to random sequences in the sample. Typically, probes on the order of 10 to 100 bases serve this purpose. Presently preferred are probes having a length of from about 15 to about 40 nucleotides, usually about 20 nucleotides.

The probes are preferably added in approximately equimolar concentration since they are expected to react stoichiometrically. More preferably, each probe is present in a concentration ranging from about 5 nanomolar (nM) to about 90 nM; preferably from about 10 nM to about 50 nM. The optimum quantity of a probe used for each reaction also varies depending on the number of cycles which must be performed. Optimum concentrations can be determined by one of ordinary skill in this art.

The stringency of conditions is generally known to those in the art to be dependent on temperature, solvent and other parameters. Perhaps the most easily controlled of these parameters is temperature and thus it is generally the reaction parameter varied in the performance of LCR. Temperatures for hybridization are usually selected to be just slightly (i.e. 1° to about 10° C.) below the melt temperature of the probes used. The hybridization conditions required for practicing this invention are similar to those of ordinary LCR and can be determined by those skilled in the art.

2. Correction of Probes

Correction mechanisms were described above, and are applied here as method steps. The preferred correction reagents are template-dependent DNA polymerases (also referred to as "target dependent DNA polymerases") that possess both 5' to 3' exonuclease and polymerizing activities. They include *Thermus aquaticus* (Taq) and other *Thermus sp.* DNA polymerases. It is preferable to use polymerases which can withstand the high temperature cycling required for LCR. If the polymerase is not thermally stable, it typically must be re-added at each LCR cycle. The polymerase can be naturally occurring or non-naturally occurring, e.g. recombinantly produced. Polymerases which can be used to practice this invention also include fragments of polymerases and polymerases having polymerization activity, with or without target dependent exonuclease activity. The polymerases need not have target dependent exonuclease activity if a separate exonucleolytic agent is also used.

Correction in this manner requires the presence in the reaction mixture of dNTP's complementary to the bases of the target. The dNTP's are commercially available from a number of sources, including Pharmacia (Piscataway, N.J.) and Bethesda Research Laboratories (Gaithersburg, Md.). As mentioned above, a subset of dNTPs may be used so that a stopbase will limit the synthesis and degradation reactions to predetermined end points. As an alternative, or in combination linkages which are resistant to hydrolysis by nucleases, such as the above exonuclease or polymerase having exonuclease activity, could be employed in the downstream probe. Examples of nuclease resistant linkages are phosphothioate and methylphosphonate linkages. These types of linkages could be incorporated into LCR probes, during the synthesis of these probes, at positions where degradation and synthesis need to be terminated, and correction could be thus limited without limiting the dNTP pool, or in addition to limiting the dNTP pool.

3. Ligation of Corrected Probes

Enzymatic ligation is the preferred method of covalently attaching the corrected probes. However, ligation can be achieved using any method of covalently attaching two probes such as photo-ligation as described in EP-A-324,616.

The conditions and reagents for the preferred enzymatic ligation step are known to those of ordinary skill in the art and are disclosed in the references mentioned in the "Background" section. Examples of ligating reagents include prokaryotic ligases such as *E. coli* ligase, T4 ligase, *Thermus thermophilus* ligase (e.g., ATCC 27634) as taught in EP-320, 308, and *Thermus aquaticus* ligase (e.g. as disclosed in WO 91/17239). The latter two ligases are preferred because they maintain their ligase activities during the thermal cycling of LCR. Absent a thermally stable ligase, the ligase must be added again each time the cycle is repeated. Also useful are eukaryotic ligases, including DNA ligase of Drosophilia, reported by Rabin, et al., *J. Biol. Chem.* 261:10637–10647 (1986).

Once ligated, the fused probe is dissociated from the target and, as with conventional LCR, the process is repeated for several cycles. The number of repeat cycles may vary from 1 to about 100, preferably from about 15 to 70. After amplification, the ligation events are determined using any of the known or disclosed methods.

Another aspect of the invention presents methods, using the above modified probes, for detecting differences in the nucleic acid sequences of the targets. This method can be used to screen for mutations, such as point mutations, insertions, deletions, and frameshifts; identify DNA polymorphisms which are useful for example for genetic mapping; and even differentiate between drug-resistant and drug-sensitive strains of microorganisms such as bacteria without the need to culture them first.

The detection is carried out, for example, by using probes with mismatched bases (WRTT) and dNTP pool which lacks the complementary bases of the mismatched bases. As an example, if the T-A base pair at position 378 in the Chlamydia MOMP 354–401 sequence (Zhang, Y. -X., et al, *Nucleic Acid Res.*, 18:1061 (1990)) (see Table 1) were changed to a C-G base pair, the correction reaction using Probes 354.1, 354.2B, 354.3B, and 354.4 could not proceed as described in Example 2. Extension of Probe 354.1 (first upstream probe) would be prevented since only dTTP is present in the reaction. Therefore, it follows that the ligation incompetent 5' end of Probe 354.2B (first downstream probe) could not be corrected. Additionally, the efficiency of extension of Probe 354.4 (second upstream probe) would be compromised as its 5' end would be mismatched with respect to target. As a result, amplification of the target sequence containing the point mutation should be eliminated or greatly reduced. It follows that depending upon the probe format used, the position of the point mutation can be varied. For example, using the terminal mismatched format, a difference in the base at position 378 or 379 could be detected since the current procedure for this format appears to require the replacement of at least one paired base beyond the mismatch as described above.

It has been reported in WO 92/02638 that polymerization independent cleavage of oligonucleotides by Taq polymerase is possible. The present invention presents a method which uses this reported activity for detecting ligated probes in the absence of polymerization.

This method uses probes with 5' extensions not hybridizable with target (analagous to FIG. 4 so as to create a "loose", overlapping end). These probes may or may not include 5' non-phosphorylated termini. According to the method, the probes are designed such that target dependent exonuclease (or polymerase with target dependent exonuclease) removes the overlap, so that the hybridized probes become adjacent and ligation can occur.

Amplification can be achieved by adding a second set of probes which can form overlaps when hybridized to the target complement. The above steps of hybridization, correction, and ligation are carried out in the presence of excess of all four probes, but no dNTP pool is used and a simple exonuclease may be used. As before, amplification involves the additional step of separating the hybridized and ligated probes from their targets or target complements, the ligated probes thus respectively serve as target complements or targets themselves for further cycles of hybridization, correction, and ligation.

V. Modes of Detection

Following correction and ligation, the LCR reaction products can be detected using methods known in the art. For example, the ligation event can be monitored by determining the presence or amount of ligated product. Since it is longer than the individual probes, this determination can be made on the basis of molecular weight. Even without labeling the probes a stained band at the correct length or molecular weight can signify the ligation event and the presence of target.

Alternatively, one or both probes of a set can be labeled using most any known technology. For example, the LCR probes can be labelled either as part of the synthetic process (using, for example, the linker arm technology disclosed in U.S. Pat. No. 4,948,882); manually using reactive groups (such as Aminomodifier II™, Clontech, Palo Alto, Calif.) added during synthesis of the probes; or enzymatically following synthesis of the probes. In one preferred embodiment, complementary Probes 1 and 3 are synthesized with one type of label, (e.g. the 5' end of Probe 1 and the 3' end of Probe 3) and complementary Probes 2 and 4 are as depected in the Figures synthesized with a second different label (e.g. the 3' end of Probe 2 and the 5' end of Probe 4). Thus, the unligated complementary probes would have only one type of label, whereas the ligated products would have both types of label. The amplified LCR reaction products can then be detected by capturing the first label with a solid phase, separating the solid phase from the solution and detecting the second label associated with the solid phase. Incomplete products, such as the individual unligated probes or complementary probe duplexes, formed during the reaction will be incapable of solid phase capture, or of label detection, or both.

An alternative labeling method incorporates a label into the dNTPs which are used for correction. Such labelling is generally a matter of conventional organic chemistry. Linkers or spacers may be used but are not essential. It is only important that the modified dNTP be incorporated opposite its complement on the target strand.

In yet another detection alternative, the ligation event is monitored by examining the nucleolytic degradation of downstream DNA sequences. As alluded to, this nucleolytic activity results in the release of mono, di, and larger nucleotide fragments. Thus, the present invention can also be used to detect the presence of a target by detecting such released fragments. Several strategies may be employed. This could be achieved, for example, by labelling the 5' end of the downstream probe with a chemical group which could be detected. The released fragment would be of a much smaller molecular weight than the probe and should be easily distinguishable using any of a number of detection methodologies, such as gel electrophoresis, or chromatographic techniques. It is generally preferred to employ a homogeneous detection system where possible. The ligation event can be detected homogenously if a fluorescent label is attached to the cleaved fragment. The spin properties of such a label will vary sufficiently between the cleaved and uncleaved state to permit detection by fluorescence polarization. Not only is this a homogeneous detection method, but it can also be used to monitor the course of an amplification reaction at intermediate stages. A specific example demonstrating detection of released fragments by fluorescence polarization is described below in Example 6.

A second homogeneous method involves the attachment of a fluorescent "donor" to the downstream probe at a position 3' of the stopbase and the attachment of a suitable quencher or blocker compound in the cleaved region at the 5' end. Of course, the reverse orientation of fluorescer and quencher is also possible. In either orientation, fluorescence is quenched or blocked in unreacted probes until correction. Upon cleavage of the 5' fragments by nucleolytic activity, the quencher and fluorescer are separated and the fluorescence can be observed.

Fluorescenced quenching as an immunoassay technique is well known in the art and is described, for example in U.S. Pat. No. 4,174,384. Examples of fluorescer/quencher pairs include the following compounds.

a) fluorescein (isothiocyanate or other derivative) with any of the following quenchers: sulforhodamine 101, sulfonyl chloride (Texas Red); succinimdyl 1-pyrenebutyrate; tetramethylrhodamine (TMR); tetramethylrhodamine isothiocyanate (TRITC); eosin-5-isothiocyanate (EITC); erythrosine-5-isothiocyanate;

b) Texas Red with malachite green isothiocyanate; and.

c) 7-amino-4-methylcoumarin-3-acetic acid, N-hydroxysuccinimidyl ester with either 4-(dimethylaminophenylazo)benzoic acid, N-hydroxysuccinimidyl ester (DABCYL NHS-ester) or 4-dimethylaminoazobenzene sulfonyl chloride (dabsyl chloride).

These and other fluorescer/quencher pairs are readily available, either commercially or from the literature.

VI. Compositions of Matter and Kits

Another aspect of the invention presents compositions of matter comprising the modified probes discussed herein that are useful for carrying out the methods disclosed herein. For example, the composition of matter may comprise one or two sets of probes, wherein at least one downstream probe is modified at its 5' end.

Reagents employed in the methods of this invention can be packaged into diagnostic kits. The kits would include the modified probes, preferably labelled. If the probes are unlabelled, the labelling reagents can also be included in the kits. The kit may also contain other suitably packaged reagents and materials needed for amplification, e.g., buffers; ligase; dNTPs; DNA polymerase with both polymerase and exonuclease activity, or a combination of polymerase and exonuclease reagents. For detection analysis, the kit may also contain for example, enzymes and solid phase extractants. The kit preferably contains instructions for conducting the assay.

VII. EXAMPLES

The invention will now be described further by way of examples. The Examples are illustrative of the invention and are not intended to limit it in any way. In the following examples, quantities of polymerase are expressed in units, as defined by the manufacturer (Molecular Biology Resources). Units of ligase enzyme are defined herein as: 1 mg of 95% purified *Thermus thermophilus* DNA ligase has a specific activity of about $1 \times 10^8$ units. While this is not precisely standardized and may vary by as much as 20%, optimization is easily within the skill of the routine practitioner.

Example 1

The following exemplifies amplification using two sets of probes, each set of probes has a downstream probe with a 5' extension consisting of three bases, and a 5' hydroxyl terminus. The 5' extensions of the first and second downstream probes are not hybridizable to each other, nor to their respective targets. (Analogous to FIG. 4)

LCR was performed for 75 cycles consisting of a 30 second incubation at 85° C. and a 40 second incubation at 55° C. in a Coy thermocycler. Reactions were set up with either 10 micrograms of human placental DNA (negative control) or 10 micrograms of human placental DNA containing various dilutions of a *Chlamydia trachomatis* positive McCoy cell lysate (positive control). A $10^{-2}$ dilution of McCoy lysate contains approximately $10^4$ genomic equivalents of *Chlamydia trachomatis* DNA. The LCR probes used are listed in Table 1 below. These probes are specific for map position 354–401 within the MOMP1 gene of *Chlamydia trachomatis* (as disclosed in Zhang, Y. -X. et al., *Nucleic Acid Res.*, 18:1061 (1990).

TABLE 1

Except where noted otherwise, the following sequences are listed in 5' to 3' direction (left to right)

| | | |
|---|---|---|
| SEQ ID NO. 1: | | Target: Chlamydia MOMP 354–401 |
| | | 5'GATAGCGAGCACAAAGAGAGCTAATTATACAATTTAGAGGTAAGAATG3' |
| | | 3'CTATCGCTCGTGTTTCTCTCGATTAATATGTTAAATCTCCATTCTTAC5' |
| SEQ ID NO. 2: | 354.1: | Carb.-GATAGCGAGCACAAAGAGAGCTAA |
| SEQ ID NO. 3: | 354.2A: | CCCTTATACAATTTAGAGGTAAGAATG-Adam. |
| SEQ ID NO. 4: | 354.3A: | CCCTTAGCTCTCTTTGTGCTCGCTATC-Carb. |

TABLE 1-continued

| | | |
|---|---|---|
| SEQ ID NO. 5: | 354.4: | Adam.-CATTCTTACCTCTAAATTGTATAA |
| SEQ ID NO. 6: | 354.2B: | TTATACAATTTAGAGGTAAGAATG-Adam. |
| SEQ ID NO. 7: | 354.3B: | TTAGCTCTCTTTGTGCTCGCTATC-Carb. |
| SEQ ID NO. 8: | 354.2C: | GTATACAATTTAGAGGTAAGAATG-Adam. |
| SEQ ID NO. 9: | 354.3C: | GTAGCTCTCTTTGTGCTCGCTATC-Carb. |
| SEQ ID NO. 10: | 354.2D: | F1-CTTATACAATTTAGAGGTAAGAATG-Adam |
| SEQ ID NO. 11: | 354.3D: | F1-CTTAGCTCTCTTTGTGCTCGCTATC-Carb |
| SEQ ID NO. 12: | | Target: Chlamydia MOMP 270–315 |
| | | 5'-TTACTTGCAAGACATTCCTCAGGCCATTAATTGCTACAGGACATCT -3' |
| | | 3'-AATGAACGTTCTGTAAGGAGTCCGGTAATTAACGATGTCCTGTAGA-5' |
| SEQ ID NO. 13: | 270.1: | Carb.-TTACTTGCAAGACATTCCTCAGG |
| SEQ ID NO. 14: | 270.2: | ACATTAATTGCTACAGGACATCT-Adam. |
| SEQ ID NO. 15: | 270.3: | ACTGAGGAATGTCTTGCAAGTAA-Carb. |
| SEQ ID NO. 16: | 270.4: | Adam-AGATGTCCTGTAGCAATTAATGG |

*.1, .2, .3, and .4 after each numerical designation indicate Probes 1, 2, 3, and 4 respectively.

Reactions were run in a buffer containing 50 mM EPPS pH 7.8, 30 mM $MgCl_2$, 20 mM KCl, 1 µM dTTP, $1\times10^{12}$ molecules each of the oligonucleotides designated 354.1, 354.2A, 354.3A, and 354.4 in Table 1, 1 unit of Thermus DNA polymerase (Molecular Biology Resources, Inc., Milwaukee, Wis.), and 5000 units of *Thermus thermophilus* DNA ligase in a final reaction volume of 50 microliters. Following amplification, reactions were diluted 1:1 with IMx® diluent buffer, and the LCR amplification products were detected via a sandwich immunoassay performed using the Abbott IMx® automated immunoassay system.

The detection was conducted as follows. In the Table, "Carb." denotes carbazole derived hapten, and "Adam." denotes adamantane derived hapten. These haptens were used to label the oligonucleotides with different labels as discussed previously. Thus, the ligated oligonucleotides would have a carbazole at one terminus and an adamantane at the other terminus for the detection by the IMx® instrument (Abbott Laboratories, Abbott Park, Ill.) using the microparticle enzyme immunoassay (MEIA) technology. The assay protocol is similar to that used in the commercially available alpha-fetoprotein assay, with the following adaptions: (1) the anti-alpha-fetoprotein antibody coated microparticles are replaced with anti-carbazole antibody coated microparticles; and (2) the conjugates of anti-alpha fetoprotein antibodies:alkaline phosphatase are replaced with the conjugates of anti-3-phenyl-1-adamantaneacetic acid antibodies:alkaline phosphatase.

The protocol for the IMx® MEIA assays is further described in EP-A-439,182, supra. In brief, the protocol is as follows. A 100 µL of the sample which has been amplified by LCR is pipetted into the sample well. 30 µL of this sample is then pipetted into the incubation well, the anticarbazole coated microparticles are added to the well. An appropriate period of incubation follows which allows the formation of a complex consisting of anticarbazole and nucleic acid sequences with the carbazole ends. After the incubation, the mixture is pipetted onto the glass fiber capture matrix of the IMx® reaction cell, and antiadamantanes conjugated to alkaline phosphatases are added. This leads to a microparticle-oligonucleotide-enzyme complex which will stay on the surface of the glass fiber capture matrix. After the removal of excess reagent in a wash step (throughout this protocol, the blotter beneath the glass fiber capture matrix absorbs reagent solutions which would otherwise overflow the glass fiber capture matrix), the glass fiber capture matrix is treated with 4-methylumbelliferyl phosphate (MUP). The surface-bound enzyme converts the nonfluorogenic MUP to 4-methylumbelliferone (MU), whose fluorescence can be measured. The numerical values given in the following examples are the rate reads of this process, expressed in counts/sec/sec (cpss). The amount of ligated probes is directly related to this rate read. This concept of MEIA readout of labeled oligonucleotides is described in European Patent Application, publication No. 357,011, published Mar. 7, 1990, "Detection and Amplification of Target Nucleic Acid Sequences," to Laffler, T. G., et al.

Duplicate assays were run and the average result is as follows:

| Target | IMx ® Rate |
|---|---|
| 0 | 11.23 ± 1 |
| $10^{-3}$ dilution | 1139.34 ± 100 |
| $10^{-4}$ dilution | 359.99 ± 21 |
| $10^{-5}$ dilution | 36.88 ± 9 |

The above result shows that as the amount target sequences increased, the number of ligated probes also increased.

Example 2

The following target amplification exemplifies the use of two sets of blunt ended probes wherein the downstream probes have 5' hydroxyl termini.

LCR was performed for 100 cycles consisting of a 30 second incubation at 85° C. and a 40 second incubation at 55° C. in a Coy thermocycler. Reactions were set up with either 1 microgram of human placental DNA (negative control) or 1 microgram of human placental DNA containing various dilutions of a *Chlamydia trachomatis* positive McCoy cell lysate (positive control). The LCR oligonucleotides used were as listed in Table 1 of Example 1 above. These oligonucleotides are specific for map position 354–401 within the MOMP1 gene of *Chlamydia trachomatis*. Reactions were run in a buffer containing 50 mM EPPS pH 7.8, 30 mM $MgCl_2$, 20 mM KCl, 1 µM dTTP, $1\times10^{12}$ molecules each of the oligonucleotides designated in Table 1 as 354.1, 354.2 B, 354.3 B, and 354.4, 1 unit of Thermus DNA polymerase, and 5000 units of *Thermus thermophilus* DNA ligase in a final reaction volume of 50 microliters.

Following amplification, reactions were diluted 1:1 with IMx® diluent buffer, and the LCR amplification products were detected via a sandwich immunoassay performed using the Abbott IMx® automated immunoassay system, as described in Example 1.

Triplicate assays were run and the average result is as follows:

| Target | IMx ® Rate |
| --- | --- |
| 0 | 17.18 ± 3 |
| $10^{-2}$ dilution | 794.83 ± 130 |
| $10^{-3}$ dilution | 81.80 ± 23 |

Example 3

The following exemplifies amplification using two sets of blunt ended probes, wherein each downstream probe has 5' hydroxyl terminus, and a one base terminal mismatch WRTT and WRTP.

LCR was performed for 70 cycles consisting of a 30 second incubation at 85° C. and a 40 second incubation at 55° C. in a Coy thermocycler. Reactions were set up with either 1 microgram of human placental DNA (negative control) or 1 microgram of human placental DNA containing a $10^{-4}$ dilution of a *Chlamydia trachomatis* positive McCoy cell lysate (positive control). The LCR oligonucleotides used are as listed in Table 1 of Example 1 above. These oligonucleotides are specific for map position 354–401 within the MOMP1 gene of *Chlamydia trachomatis*. Reactions were run in a buffer containing 50 mM EPPS pH 7.8, 30 mM $MgCl_2$, 20 mM KCl, 1 µM dTTP, $1 \times 10^{12}$ molecules each of the oligonucleotides designated in Table 1 as 354.1, 354.2C, 354.3C, and 354.4, 1 unit of Thermus DNA polymerase, and 5000 units of *Thermus thermophilus* DNA ligase in a final reaction volume of 50 microliters.

Following amplification, reactions were diluted 1:1 with IMx® diluent buffer, and the LCR amplification products were detected via a sandwich immunoassay using the Abbott IMx® automated immunoassay system, as described in Example 1.

Duplicate assays were run and the average result is shown below:

| Target | IMx ® Rate |
| --- | --- |
| 0 | 11.18 ± 1 |
| $10^{-4}$ dilution | 1648.87 ± 120 |

Example 4

The following amplification used blunt ended probes of the same format as those used in Example 3, but with different nucleic acid sequences.

LCR was performed for 40, 50, or 60 cycles consisting of a 30 second incubation at 85° C. and a 25 second incubation at 55° C. in a Perkin-Elmer 480 thermocycler (Perkin-Elmer, Norwalk, Conn.). Reactions were set up with either 1 microgram of human placental DNA (negative control) or 1 microgram of human placental DNA containing $10^2$ *Chlamydia trachomatis* elementary bodies (positive control). The LCR oligonucleotides used are as listed in Table 1 of Example 1 above. These oligonucleotides are specific for map position 270–315 within the MOMP1 gene of Chlamydia trachomatis. Reactions were run in a buffer containing 50 mM EPPS pH 7.8, 30 mM $MgCl_2$, 20 mM KCl, 1 µM dCTP, $1 \times 10^{12}$ molecules each of the oligonucleotides designated in Table 1 as 270.1, 270.2, 270.3, and 270.4, 2 unit of Thermus DNA polymerase, and 5000 units of *Thermus thermophilus* DNA ligase in a final reaction volume of 50 microliters.

Following amplification, reactions were diluted 1:1 with IMx® diluent buffer, and the LCR amplification products were detected via a sandwich immunoassay performed using the Abbott IMx® automated immunoassay system, as described in Example 1.

Duplicate assays were run and the average result is as follows:

| | Target Molecules | IMx ® Rate |
| --- | --- | --- |
| 40 cycles: | 0 | 59.42 ± 5 |
| | $10^2$ | 1750.15 ± 45 |
| 50 cycles: | 0 | 11.02 ± 1 |
| | $10^2$ | 2576.55 ± 20 |
| 60 cycles: | 0 | 12.72 ± 0 |
| | $10^2$ | 2629.98 ± 7 |

Example 5

The following example used two sets of probes wherein each downstream probe has a 5' hydroxyl terminus and a 5' extension consisting of one base. These extensions are hybridizable to each other but not to their respective targets. These probes were used to detect hepatitis B virus (HBV) specific sequences in serum samples.

The HBV specific nucleic acid sequences used for the probes within this example were mapped according to Ono Y. et al., *Nucleic Acid Res.*, 11, 1747–1757 (1983). Except otherwise noted, the sequences are listed in 5' to 3' direction (left to right) where "F" indicates the label Fluorescein-5-isothiocyanate (FITC isomer, Molecular Probes Inc.) and "B" represents a Biotin molecule (Biotin-xx-NHS ester, Clontech Laboratories Inc). The probe sequence is base 666 to base 709 of HBV subtype ADW.

TABLE 2

| SEQ ID NO. 17: | 666:1 F-CTCTTGGCTCAGTTTACTAGTG |
| --- | --- |
| SEQ ID NO. 18: | 666:2 ACATTTGTTCAGTGGTTCGTAG-B |
| SEQ ID NO. 19: | 666:3 TCACTAGTAAACTGAGCCAAGAG-F |
| SEQ ID NO. 20: | 666:4 B-CTACGAACCACTGAACAAATG |
| SEQ ID NO. 21: | TARGET: |
| | 5'-CTCTTGGCTCAGTTTACTAGTGCCATTTGTTCAGTGGTTCGTAG-3' |
| | 3'-GAGAACCGAGTCAAATGATCACGGTAAACAAGTCACCAAGCATC-5' |

Reaction were set up with either HBV negative serum (negative control) or serum containing either $1.4 \times 10^5$ or $1.0 \times 10^3$ HBV genomes. The serum samples were treated with Proteinase K (50° C., 3 hrs) and heated at 100° C. for 15 minutes.

The modified LCR was performed for 55 cycles consisting of a 30 seconds incubation at 85° C. and 40 seconds incubation at 50° C. in a Perkin-Elmer 480 thermocycler. Reaction were run in a buffer containing 50 mM EPPS pH 7.8, 30 mM $MgCl_2$, 20 mM KCl, 1 µM each of dCTP and dGTP, $1\times10^{12}$ molecules each of the oligonucleotides designated 666:1, 666:2, 666:3 and 666:4, 2 units of Thermus DNA Polymerase, and 5000 units of *Thermus thermophilus* DNA ligase in a final reaction volume of 50 microliters. Following amplification, reactions were diluted 1:1 with $H_2O$ and specific ligation products were detected via a sandwich immunoassay on Abbott IMx® automated immunoassay system. The MEIA protocol for detecting the ligated probes was similar to that used in Example 1 above, except that the following were used: (1) anti-biotin antibody coated microparticles; and (2) the conjugates of anti-fluorescein antibodies:alkaline phosphatase. The results are shown below:

| Target Molecules | IMx ® Rates |
| --- | --- |
| 0 | 13.37 |
| $1 \times 10^3$ | 32.19 |
| $1.4 \times 10^5$ | 331.24 |

Example 6

The following target amplification exemplifies the detection of released fragments of hybridized probes. It used downstream probes with a one base 5' extensions which contained a detectable fluorescein group at their 5' termini. These extensions are not hybridizable to each other and their respective targets.

LCR was performed for 85 cycles consisting of a 30 second incubation at 85° C. and a 40 second incubation at 55° C. in a Coy thermocycler. Reactions were set up with either 1 microgram of human placental DNA (negative control) or 1 microgram of human placental DNA containing a $10^{31\ 2}$ dilutions of a *Chlamydia trachomatis* positive McCoy cell lysate (positive control). The LCR oligonucleotides used were as listed in Table 1 of Example 1 above. These oligonucleotides are specific for map position 354–401 within the MOMP1 gene of *Chlamydia trachomatis*. Reactions were run in a buffer containing 50 mM EPPS pH 7.8, 30 mM $MgCl_2$, 20 mM KCl, 1 µM dTTP, $1\times10^{12}$ molecules each of the oligonucleotides designated in Table 1 as 354.1, 354.2 D, 354.3 D, and 354.4, 1 unit of Thermus DNA polymerase, and 5000 units of *Thermus thermophilus* DNA ligase in a final reaction volume of 50 microliters.

Following amplification, reactions were diluted 1:1 with IMx® diluent buffer, and the LCR amplification products were detected via a sandwich immunoassay performed using the Abbott IMx® automated immunoassay system, as described in Example 1.

Duplicate assays were run, and the average result is as follows:

| TARGET | IMx ® Rates |
| --- | --- |
| 0 | 146.88 ± 95 |
| $10^{-2}$ dilution | 2030.83 ± 50 |

The released fragments were detected using fluorescence polarization technique using an Abbott TDx® fluorescence polarization immunoassay analyzer (Abbott Laboratories, Abbott Park, Ill.). Amplification products remaining from the IMx® detection assay were diluted to 200 µL with IMx® diluent buffer and the fluorescence polarization values for each sample were determined.

The average result is as follows:

| TARGET | TDx ® Results |
| --- | --- |
| 0 | 201.9 ± 0.5 |
| $10^{-2}$ dilution | 93.07 ± 3 |

The polarization of a fluorescent compound is inversely proportional to the size of the molecule to which it is attached. Therefore, the polarization of a fluorescent molecule attached to an intact oligonucleotide would be expected to be greater than the polarization of the fluorophore attached to a smaller molecular weight degradation product derived from the oligonucleotide, in this case, the released fragments. It follows that a decrease in the polarization value would be indicative of the correction of the downstream probes.

Although the foregoing invention has been described in some detail by way of illustration and examples for purposes of clarity and understanding, it will be obvious that the above methods, compositions, and kits can be used in reducing target independent amplification in other nucleic acid amplification technologies besides that of LCR. Further, various modifications and changes which are within the skill of those skilled in the art are considered to fall within the scope of the appended claims. Future technological advancements which allow for obvious changes in the basic invention herein are also within the claims.

We claim:

1. A method for assaying a target nucleic acid sequence comprising the steps of:
   (a) under hybridizing conditions exposing a sample suspected of containing the target nucleic acid sequence in single stranded form to an excess of a first set of oligonucleotides comprising a first upstream probe and a first downstream probe, both probes having sequences substantially complementary to portions of a target nucleic acid sequence, the 3' terminus of the first upstream probe hybridizing proximate to the 5' terminus of the first downstream probe, wherein the 5' end of the first downstream probe is modified to be ligation incompetent absent correction, thereby hybridizing the first set of oligonucleotides to the target nucleic acid sequence, if present;
   (b) correcting the 5' end of the downstream probe when the downstream probe is hybridized to target, said correction including nucleolytic degradation of said 5' end, whereby the correction renders this 5' end ligation competent;
   (c) ligating the corrected downstream probe to the upstream probe to form a ligated product; and
   (d) determining to what extent the correction and ligation steps occur as a measure of the target nucleic acid in the sample.

2. The method of claim 1, wherein determining the extent of correction and ligation comprises separating ligated product from unligated probes and determining the amount of ligated product formed.

3. The method of claim 1, wherein determining the extent of correction and ligation comprises monitoring the release of cleaved fragments from the 5' end of said downstream probe, wherein said cleaving is performed by a template-dependent polymerase having 5' to 3' nucleolytic activity.

4. The method of claim 1, wherein said ligation incompetent 5' end comprises a non-phosphorylated 5' terminus and wherein said correction step comprises cleaving the terminal nucleoside to create a new 5' phosphorylated terminus on said downstream probe.

5. The method of claim 4, wherein said correction step further comprises extending the 3' terminus of said upstream probe by the addition of one or more nucleotide triphosphates in a template-dependent manner to bring said extended 3' terminus adjacent to said newly created 5' phosphorylated terminus.

6. The method of claim 5, wherein both said cleaving and extending steps are performed by a template-dependent polymerase having 5' to 3' nucleolytic activity.

7. The method of claim 4, wherein determining the extent of correction and ligation comprises separating ligated product from unligated probes and determining the amount of ligated product formed.

8. The method of claim 4, wherein said terminal nucleotide of the downstream probe carries a label, and wherein said cleaving is performed by a template-dependent polymerase having 5' to 3' nucleolytic activity and further wherein said determining the extent of correction and ligation comprises monitoring the release of label from the downstream probe.

9. The method of claim 8 wherein said label is a fluorescent label and said monitoring comprises fluorescence polarization.

10. The method of claim 1, wherein the ligation incompetent 5' end comprises at least one nucleotide base in said 5' end which is mismatched with respect to the target sequence to which it hybridizes, and wherein said correction step comprises cleaving the mismatched nucleotide to create a new 5' phosphorylated terminus on said downsteam probe.

11. The method of claim 10, wherein said correction step further comprises extending the 3' terminus of said upstream probe by the addition of one or more nucleotide triphosphates in a template-dependent manner to bring said extended 3' terminus adjacent to said newly created 5' phosphorylated terminus.

12. The method of claim 11, wherein both said cleaving and extending steps are performed by a template-dependent polymerase having 5' to 3' nucleolytic activity.

13. The method of claim 10, wherein said at least one mismatched base is positioned at the 5' terminal nucleotide.

14. The method of claim 10, wherein said at least one mismatched base is positioned within 1 to about 5 nucleotides internal of said 5' terminal nucleotide.

15. The method of claim 13 or 14, wherein said cleaving step includes cleaving a nucleotide adjacent the mismatched nucleotide on its 3' side.

16. The method of claim 10, wherein the ligation incompetent 5' end of said downstream probe further comprises a non-phosphorylated 5' terminus.

17. The method of claim 10, wherein determining the extent of correction and ligation comprises separating ligated product from unligated probes and determining the amount of ligated product formed.

18. The method of claim 10, wherein said cleaving is performed by a template-dependent polymerase having 5' to 3' nucleolytic activity, and wherein the cleaved portion of the 5' end of the downstream probe carries a label, and further wherein said determining the extent of correction and ligation comprises monitoring the release of label from the downstream probe.

19. The method of claim 18 wherein said label is a fluorescent label and said monitoring comprises fluorescence polarization.

20. The method of claim 10, wherein the upstream and downstream probes hybridize to target such that the mismatched 5' end of downstream probe overlaps the 3' end of the upstream probe by at least one overlapping base, and wherein the correction step comprises removal of said at least one overlapping base to create a new 5' phosphorylated terminus such that the newly created 5' terminus of the downstream probe abuts the 3' end of the upstream probe without extending the upstream probe, so that the two probes can be directly ligated.

21. The method of claim 20, wherein the mismatched 5' end of said downstream probe further comprises a non-phosphorylated 5' terminus.

22. The method of claim 1, further comprising an excess of a second set of oligonucleotides comprising a second upstream probe and a second downstream probe, both probes having sequences substantially complementary to the first downstream probe and first upstream probes, respectively, the 3' terminus of the second upstream probe being hybridized proximate to the 5' terminus of the second downstream probe, and wherein said hybridization, correction and ligation steps (a–c) are repeated to effect an amplification of the target nucleic acid sequence.

23. The method of claim 22, wherein the ligation incompetent 5' end of said first downstream probe comprises a non-phosphorylated 5' terminus and wherein said correction step comprises cleaving the terminal nucleoside to create a new 5' phosphorylated terminus on said downstream probe.

24. The method of claim 23, wherein the 5' end of the second downstream probe is also modified to be ligation incompetent absent correction, and wherein said correction step includes nucleolytic degradation of the 5' end of said second downstream probe to create a new phosphorylated 5' terminus, whereby the correction step renders the 5' ends of both downstream probes ligation competent.

25. The method of claim 24, wherein said modification of the second downstream probe is selected from: (a) a non-phosphorylated 5' terminus; and (b) at least one nucleotide base in the 5' end which is mismatched with respect to the template sequence to which it hybridizes; and wherein said correcting step includes cleaving said non-phosphorylated nucleotide or said mismatched nucleotide.

26. The method of claim 24, wherein said correction step further comprises extending the 3' terminus of both said upstream probes by the addition of one or more nucleotide triphosphates in a template-dependent manner to bring said extended 3' termini adjacent to said newly created 5' phosphorylated termini.

27. The method of claim 26, wherein both said cleaving and extending steps are performed by a template-dependent polymerase having 5' to 3' nucleolytic activity.

28. The method of claim 24, wherein determining the extent of correction and ligation comprises separating ligated product from unligated probes and determining the amount of ligated product formed.

29. The method of claim 24, wherein said terminal nucleotide of the downstream probe carries a label, and wherein said cleaving is performed by a template-dependent polymerase having 5' to 3' nucleolytic activity and further wherein said determining the extent of correction and ligation comprises monitoring the release of label from the downstream probe.

30. The method of claim 22, wherein the ligation incompetent 5' end of said first downstream probe comprises at least one nucleotide base in said 5' end which is mismatched with respect to the template sequence to which it hybridizes, and wherein said correction step comprises cleaving the mismatched nucleotide to create a new 5' phosphorylated terminus on said downsteam probe.

31. The method of claim 30, wherein the 5' end of the second downstream probe is also modified to be ligation incompetent absent correction, and wherein said correction step includes nucleolytic degradation of the 5' end of said second downstream probe to create a new phosphorylated 5' terminus, whereby the correction step renders the 5' ends of both downstream probes ligation competent.

32. The method of claim 31, wherein said modification of the second downstream probe is selected from: (a) a non-phosphorylated 5' terminus; or (b) at least one nucleotide base in the 5' end which is mismatched with respect to the template sequence to which it hybridizes; and wherein said correcting step includes cleaving said non-phosphorylated nucleotide or said mismatched nucleotide.

33. The method of claim 31, wherein said correction step further comprises extending the 3' terminus of both said upstream probes by the addition of one or more nucleotide triphosphates in a template-dependent manner to bring said extended 3' termini adjacent to said newly created 5' phosphorylated termini.

34. The method of claim 32, wherein the 5' end of said first downstream probe further comprises a non-phosphorylated 5' terminus.

35. The method of claim 33, wherein both said cleaving and extending steps are performed by a template-dependent polymerase having 5' to 3' nucleolytic activity.

36. The method of claim 32, wherein the at least one mismatched base of one or both of said downstream probes is positioned at the 5' terminal nucleotide.

37. The method of claim 32, wherein the at least one mismatched base of one or both of said downstream probes is positioned within 1 to about 5 nucleotides internal of said 5' terminal nucleotide.

38. The method of claim 36 or 37, wherein said cleaving step includes cleaving a nucleotide adjacent the mismatched nucleotide on its 3' side.

39. The method of claim 31, wherein determining the extent of correction and ligation comprises separating ligated product from unligated probes and determining the amount of ligated product formed.

40. The method of claim 31, wherein said terminal nucleotide of the downstream probe carries a label, and wherein said cleaving is performed by a template-dependent polymerase having 5' to 3' nucleolytic activity, and further wherein said determining the extent of correction and ligation comprises monitoring the release of label from the downstream probe.

41. A composition of matter comprising:
  (a) a first set of oligonucleotides comprising a first upstream probe and a first downstream probe, both probes having sequences substantially complementary to portions of a target nucleic acid sequence, the 3' terminus of the first upstream probe hybridizing proximate to the 5' terminus of the first downstream probe; and
  (b) a second set of oligonucleotides comprising a second upstream probe and a second downstream probe, both probes having sequences substantially complementary to the first downstream probe and first upstream probes, respectively, the 3' terminus of the second upstream probe being hybridized proximate to the 5' terminus of the second downstream probe;
  wherein the 5' end of at least one of the first or second downstream probes is modified to be ligation incompetent absent correction and wherein there is a gap between the 3' terminus of the hybridized upstream probe and the 5' terminus of the hybridized downstream probe, or the 5' terminus of the downstream probe overlaps the 3' terminus of the upstream probe or the downstream probe comprises a non-phosphorylated 5' terminus.

42. The composition of claim 41, wherein the ligation incompetent 5' end comprises a non-phosphorylated 5' terminus.

43. The composition of claim 42, wherein the non-phosphorylated 5' terminus is selected from the group consisting of hydroxyl, hydryl, and amino.

44. The composition of claim 42, wherein the non-phosphorylated 5' terminus includes a label selected from the group consisting of fluorescent labels, radioisotopic labels, chemiluminescent labels, chromophore labels and hapten labels.

45. The composition of claim 41, wherein the ligation incompetent 5' end comprises at least one nucleotide base in said 5' end which is mismatched with respect to the target sequence to which it hybridizes or with respect to the complementary upstream probe.

46. The composition of claim 45, wherein said at least one mismatched base is positioned at the 5' terminal nucleotide.

47. The composition of claim 45, further comprising a non-phosphorylated 5' terminus.

48. The composition of claim 41, wherein both downstream probes have ligation incompetent 5' ends.

49. A kit comprising in one or more suitable containers:
  (a) a set of oligonucleotides comprising an upstream probe and a downstream probe, both probes having sequences substantially complementary to portions of a target nucleic acid sequence, the 3' terminus of the first upstream probe hybridizing proximate to the 5' terminus of the first downstream probe, wherein the 5' end of said downstream probes is modified to be ligation incompetent absent correction and wherein there is a gap between the 3' terminus of the hybridized upstream probe and the 5' terminus of the hybridized downstream probe, or the 5' terminus of the downstream probe overlaps the 3' terminus of the upstream probe or the downstream probe comprises a non-phosphorylated 5' terminus;
  (b) one or more correcting reagents for correcting the ligation incompetent downstream probe in a target-dependent manner to render the downstream probe ligatable and for rendering the upstream and downstream probes ligation competent wherein said correcting reagents comprise one or more enzymes having cleaving or cleaving and extending activity; and
  (c) a ligating reagent for ligating the corrected downstream probe to the upstream probe.

50. The kit of claim 49, wherein said ligation incompetent 5' end comprises a non-phosphorylated 5' terminus.

51. The kit of claim 49, wherein the ligation incompetent 5' end comprises at least one nucleotide base in said 5' end which is mismatched with respect to the target sequence to which it hybridizes.

52. The kit of claim 51, further comprising a non-phosphorylated 5' terminus.

53. The kit of claim 51, wherein said correcting reagent comprises an agent having target-dependent 5' to 3' nucleolytic activity.

54. The kit of claim 53 wherein said correcting reagent comprises a target-dependent polymerase.

55. The kit of claim 49, further comprising a second set of oligonucleotides comprising a second upstream probe and a second downstream probe, both probes having sequences substantially complementary to the first downstream probe and first upstream probes, respectively, the 3' terminus of the second upstream probe being hybridized proximate to the 5' terminus of the second downstream probe.

56. The kit of claim 55, wherein the ligation incompetent 5' end on at least one of said downstream probes comprises a non-phosphorylated 5' terminus.

57. The kit of claim 55, wherein the ligation incompetent 5' end on at least one of said downstream probes comprises at least one nucleotide base in said 5' end which is mismatched with respect to the target sequence to which it hybridizes.

58. The kit of claim 57, wherein the ligation incompetent 5' end on said at least one downstream probe further comprises a non-phosphorylated 5' terminus.

59. The kit of claim 55, wherein said correcting reagent comprises a target-dependent polymerase having target-dependent 5' to 3' nucleolytic activity.

* * * * *

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 48 base pairs
        ( B ) TYPE: nucleic acid
        ( C ) STRANDEDNESS: double
        ( D ) TOPOLOGY: linear ( i i ) MOLECULE TYPE: DNA (genomic)

(iii) HYPOTHETICAL: NO (vi) ORIGINAL SOURCE:
    (A) ORGANISM: Chlamydia trachomatis (viii) POSITION IN GENOME:
    (B) MAP POSITION: 354-401

(xi) SEQUENCE DESCRIPTION: SEQ ID NO:1:

GATAGCGAGC ACAAAGAGAG CTAATTATAC AATTTAGAGG TAAGAATG        48

(2) INFORMATION FOR SEQ ID NO:2:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: synthetic DNA (iii) HYPOTHETICAL: NO (ix) FEATURE:
        (A) NAME/KEY: misc_feature
        (B) LOCATION: 1

(xi) SEQUENCE DESCRIPTION: SEQ ID NO:2:

GATAGCGAGC ACAAAGAGAG CTAA        24

(2) INFORMATION FOR SEQ ID NO:3:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: synthetic DNA (iii) HYPOTHETICAL: NO (ix) FEATURE:
        (A) NAME/KEY: misc_feature
        (B) LOCATION: 27

(xi) SEQUENCE DESCRIPTION: SEQ ID NO:3:

CCCTTATACAAT TTAGAGGTAA GAATG        27

(2) INFORMATION FOR SEQ ID NO:4:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: synthetic DNA (iii) HYPOTHETICAL: NO (ix) FEATURE:
        (A) NAME/KEY: misc_feature
        (B) LOCATION: 27

(xi) SEQUENCE DESCRIPTION: SEQ ID NO:4:

CCCTTAGCTC TCTTTGTGCT CGCTATC        27

(2) INFORMATION FOR SEQ ID NO:5:

(i) SEQUENCE CHARACTERISTICS:

( A ) LENGTH: 24 base pairs
                    ( B ) TYPE: nucleic acid
                    ( C ) STRANDEDNESS: single
                    ( D ) TOPOLOGY: linear ( i i ) MOLECULE TYPE: synthetic DNA ( i i i ) HYPOTHETICAL: NO ( i x ) FEATURE:
                    ( A ) NAME/KEY: misc_feature
                    ( B ) LOCATION: 1

( x i ) SEQUENCE DESCRIPTION: SEQ ID NO:5:

CATTCTTACC TCTAAATTGT ATAA                                                                              24

( 2 ) INFORMATION FOR SEQ ID NO:6:

( i ) SEQUENCE CHARACTERISTICS:
                    ( A ) LENGTH: 24 base pairs
                    ( B ) TYPE: nucleic acid
                    ( C ) STRANDEDNESS: single
                    ( D ) TOPOLOGY: linear ( i i i ) HYPOTHETICAL: NO ( i x ) FEATURE:
                    ( A ) NAME/KEY: misc_feature
                    ( B ) LOCATION: 24

( x i ) SEQUENCE DESCRIPTION: SEQ ID NO:6:

TTATACAATT TAGAGGTAAG AATG                                                                              24

( 2 ) INFORMATION FOR SEQ ID NO:7:

( i ) SEQUENCE CHARACTERISTICS:
                    ( A ) LENGTH: 24 base pairs
                    ( B ) TYPE: nucleic acid
                    ( C ) STRANDEDNESS: single
                    ( D ) TOPOLOGY: linear ( i i ) MOLECULE TYPE: synthetic DNA ( i i i ) HYPOTHETICAL: NO ( i x ) FEATURE:
                    ( A ) NAME/KEY: misc_feature
                    ( B ) LOCATION: 24

( x i ) SEQUENCE DESCRIPTION: SEQ ID NO:7:

TTAGCTCTCT TTGTGCTCGC TATC                                                                              24

( 2 ) INFORMATION FOR SEQ ID NO:8:

( i ) SEQUENCE CHARACTERISTICS:
                    ( A ) LENGTH: 24 base pairs
                    ( B ) TYPE: nucleic acid
                    ( C ) STRANDEDNESS: single
                    ( D ) TOPOLOGY: linear ( i i ) MOLECULE TYPE: synthetic DNA ( i i i ) HYPOTHETICAL: NO ( i x ) FEATURE:
                    ( A ) NAME/KEY: misc_feature
                    ( B ) LOCATION: 24

( x i ) SEQUENCE DESCRIPTION: SEQ ID NO:8:

GTATACAATT TAGAGGTAAG AATG                                                                              24

( 2 ) INFORMATION FOR SEQ ID NO:9:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( i i ) MOLECULE TYPE: synthetic DNA ( i i i ) HYPOTHETICAL: NO ( i x ) FEATURE:
  ( A ) NAME/KEY: misc_feature
  ( B ) LOCATION: 24

( x i ) SEQUENCE DESCRIPTION: SEQ ID NO:9:

GTAGCTCTCT TTGTGCTCGC TATC  24

( 2 ) INFORMATION FOR SEQ ID NO:10:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: synthetic DNA ( i i i ) HYPOTHETICAL: NO ( i x ) FEATURE:
    ( A ) NAME/KEY: misc_feature
    ( B ) LOCATION: 1

( i x ) FEATURE:
    ( A ) NAME/KEY: misc_feature
    ( B ) LOCATION: 25

( x i ) SEQUENCE DESCRIPTION: SEQ ID NO:10:

CTTATACAAT TTAGAGGTAA GAATG  25

( 2 ) INFORMATION FOR SEQ ID NO:11:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: synthetic DNA ( i i i ) HYPOTHETICAL: NO ( i x ) FEATURE:
    ( A ) NAME/KEY: misc_feature
    ( B ) LOCATION: 1

( i x ) FEATURE:
    ( A ) NAME/KEY: misc_feature
    ( B ) LOCATION: 25

( x i ) SEQUENCE DESCRIPTION: SEQ ID NO:11:

CTTAGCTCTC TTTGTGCTCG CTATC  25

( 2 ) INFORMATION FOR SEQ ID NO:12:

( i ) SEQUENCE CHARACTERISTICS:
    ( A ) LENGTH: 46 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( v i ) ORIGINAL SOURCE:
    ( A ) ORGANISM: Chlamydia trachomatis ( v i i i ) POSITION IN GENOME:
    ( B ) MAP POSITION: 270-315

( x i ) SEQUENCE DESCRIPTION: SEQ ID NO:12:

TTACTTGCAA GACATTCCTC AGGCCATTAA TTGCTACAGG ACATCT      46

( 2 ) INFORMATION FOR SEQ ID NO:13:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: synthetic DNA ( i i i ) HYPOTHETICAL: NO ( i x ) FEATURE:
        ( A ) NAME/KEY: misc_feature
        ( B ) LOCATION: 1

( x i ) SEQUENCE DESCRIPTION: SEQ ID NO:13:

TTACTTGCAA GACATTCCTC AGG      23

( 2 ) INFORMATION FOR SEQ ID NO:14:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: synthetic DNA ( i i i ) HYPOTHETICAL: NO ( i x ) FEATURE:
        ( A ) NAME/KEY: misc_feature
        ( B ) LOCATION: 23

( x i ) SEQUENCE DESCRIPTION: SEQ ID NO:14:

ACATTAATTG CTACAGGACA TCT      23

( 2 ) INFORMATION FOR SEQ ID NO:15:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: synthetic DNA ( i i i ) HYPOTHETICAL: NO ( i x ) FEATURE:
        ( A ) NAME/KEY: misc_feature
        ( B ) LOCATION: 23

( x i ) SEQUENCE DESCRIPTION: SEQ ID NO:15:

ACTGAGGAAT GTCTTGCAAG TAA      23

( 2 ) INFORMATION FOR SEQ ID NO:16:

( i ) SEQUENCE CHARACTERISTICS:
        ( A ) LENGTH: 23 base pairs ( B ) TYPE: nucleic acid
           ( C ) STRANDEDNESS: single
           ( D ) TOPOLOGY: linear ( i i ) MOLECULE TYPE: synthetic DNA ( i i i ) HYPOTHETICAL: NO ( i x ) FEATURE:
           ( A ) NAME/KEY: misc_feature
           ( B ) LOCATION: 1

( x i ) SEQUENCE DESCRIPTION: SEQ ID NO:16:

AGATGTCCTG TAGCAATTAA TGG                23

( 2 ) INFORMATION FOR SEQ ID NO:17:

( i ) SEQUENCE CHARACTERISTICS:
           ( A ) LENGTH: 22 base pairs
           ( B ) TYPE: nucleic acid
           ( C ) STRANDEDNESS: single
           ( D ) TOPOLOGY: linear ( i i ) MOLECULE TYPE: synthetic DNA ( i i i ) HYPOTHETICAL: NO ( i x ) FEATURE:
           ( A ) NAME/KEY: misc_feature
           ( B ) LOCATION: 1

( x i ) SEQUENCE DESCRIPTION: SEQ ID NO:17:

CTCTTGGCTC AGTTTACTAG TG                22

( 2 ) INFORMATION FOR SEQ ID NO:18:

( i ) SEQUENCE CHARACTERISTICS:
           ( A ) LENGTH: 22 base pairs
           ( B ) TYPE: nucleic acid
           ( C ) STRANDEDNESS: single
           ( D ) TOPOLOGY: linear ( i i ) MOLECULE TYPE: synthetic DNA ( i i i ) HYPOTHETICAL: NO ( i x ) FEATURE:
           ( A ) NAME/KEY: misc_feature
           ( B ) LOCATION: 22

( x i ) SEQUENCE DESCRIPTION: SEQ ID NO:18:

ACATTTGTTC AGTGGTTCGT AG                22

( 2 ) INFORMATION FOR SEQ ID NO:19:

( i ) SEQUENCE CHARACTERISTICS:
           ( A ) LENGTH: 23 base pairs
           ( B ) TYPE: nucleic acid
           ( C ) STRANDEDNESS: single
           ( D ) TOPOLOGY: linear ( i i ) MOLECULE TYPE: synthetic DNA ( i i i ) HYPOTHETICAL: NO ( i x ) FEATURE:
           ( A ) NAME/KEY: misc_feature
           ( B ) LOCATION: 23

( x i ) SEQUENCE DESCRIPTION: SEQ ID NO:19:

TCACTAGTAA ACTGAGCCAA GAG                23

( 2 ) INFORMATION FOR SEQ ID NO:20:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: synthetic DNA ( i i i ) HYPOTHETICAL: NO ( i x ) FEATURE:
        ( A ) NAME/KEY: misc_feature
        ( B ) LOCATION: 1

( x i ) SEQUENCE DESCRIPTION: SEQ ID NO:20:

```
CTACGAACCA CTGAACAAAT G                                              21
```

( 2 ) INFORMATION FOR SEQ ID NO:21:

( i ) SEQUENCE CHARACTERISTICS:
        ( A ) LENGTH: 44 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Hepatitis B virus ( v i i i ) POSITION IN GENOME:
        ( B ) MAP POSITION: 666-712

( x i ) SEQUENCE DESCRIPTION: SEQ ID NO:21:

```
CTCTTGGCTC AGTTTACTAG TGCCATTTGT TCAGTGGTTC GTAG                     44
```